US009255124B2

(12) United States Patent
Maclean

(10) Patent No.: US 9,255,124 B2
(45) Date of Patent: Feb. 9, 2016

(54) MODIFICATIONS OF PEPTIDE COMPOSITIONS TO INCREASE STABILITY AND DELIVERY EFFICIENCY

(75) Inventor: Derek Maclean, Los Altos, CA (US)

(73) Assignee: KAI PHARMACEUTICALS, INC., South San Francisco, CA (US)

( * ) Notice: Subject to any disclaimer, the term of this patent is extended or adjusted under 35 U.S.C. 154(b) by 892 days.

(21) Appl. No.: 13/305,685

(22) Filed: Nov. 28, 2011

(65) Prior Publication Data

US 2012/0178138 A1    Jul. 12, 2012

Related U.S. Application Data

(62) Division of application No. 12/017,985, filed on Jan. 22, 2008, now Pat. No. 8,067,532.

(60) Provisional application No. 60/881,419, filed on Jan. 19, 2007, provisional application No. 60/945,285, filed on Jun. 20, 2007.

(51) Int. Cl.
*C07K 7/00* (2006.01)
*A61K 38/10* (2006.01)
*A61K 47/48* (2006.01)

(52) U.S. Cl.
CPC . *C07K 7/00* (2013.01); *A61K 38/10* (2013.01); *A61K 47/48246* (2013.01); *A61K 47/48315* (2013.01)

(58) Field of Classification Search
CPC ........................................................ C07K 7/00
See application file for complete search history.

(56) References Cited

U.S. PATENT DOCUMENTS

| | | | |
|---|---|---|---|
| 5,783,405 A * | 7/1998 | Mochly-Rosen et al. ...... 506/10 |
| 6,165,977 A * | 12/2000 | Mochly-Rosen ................. 506/9 |
| 6,306,993 B1 | 10/2001 | Rothbard et al. |
| 6,316,003 B1 * | 11/2001 | Frankel et al. ........... 424/196.11 |
| 6,855,693 B2 | 2/2005 | Mochly-Rosen et al. |
| 6,933,275 B2 | 8/2005 | Mochly-Rosen et al. |
| 7,265,092 B2 | 9/2007 | Li |
| 8,067,532 B2 | 11/2011 | MacLean |
| 2002/0150984 A1 * | 10/2002 | Mochly-Rosen et al. ... 435/69.1 |
| 2002/0168354 A1 * | 11/2002 | Mochly-Rosen ............ 424/94.5 |
| 2003/0223981 A1 * | 12/2003 | Mochly-Rosen et al. ... 424/94.5 |
| 2004/0009919 A1 * | 1/2004 | Mochly-Rosen et al. ...... 514/12 |
| 2004/0009922 A1 | 1/2004 | Mochly-Rosen |
| 2004/0204364 A1 | 10/2004 | Mochly-Rosen et al. |
| 2006/0153867 A1 | 7/2006 | Li |
| 2009/0042769 A1 | 2/2009 | MacLean |

FOREIGN PATENT DOCUMENTS

| | | |
|---|---|---|
| WO | WO 98/52614 A2 | 11/1998 |
| WO | WO 02/28408 A2 | 4/2002 |
| WO | WO 02/057413 A2 | 7/2002 |
| WO | WO 03/089456 A2 | 10/2003 |
| WO | WO 03/089457 A2 | 10/2003 |
| WO | WO 03/103698 A1 | 12/2003 |
| WO | WO 2007/040711 A2 | 4/2007 |

OTHER PUBLICATIONS

Zorko (Advanced Drug Delivery Reviews 57(4), 529-545, 2005).*
Saalik (Bioconjugate Chemistry 15(6), 1246-53, 2004).*
Futaki (Int J. Pharm 245, 1-7, 2002).*
Daria Mochly-Rosen, List of peptides provided for experimental use sent to Dr. Nicholas Webster, University of California, San Diego, San Diego, California, U.S., Feb. 25, 1996.
Che-Hong Chen, List of peptides provided for experimental use sent to Dr. Sue Heffelfinger, University of Cincinnati, Cincinnati, Ohio, U.S., Apr. 3, 1996.
Daria Mochly-Rosen, List of peptides provided for experimental use sent to Dr. James A. Fagin, University of Cincinnati, Cincinnati Ohio, U.S., Apr. 3, 1996.
Che-Hong Chen, List of peptides provided for experimental use and related correspondence sent to and from Dr. Aileen Long, Trinity College, St. James' Hospital, Dublin, Ireland, Jul. 23, 1996.
Che-Hong Chen, List of peptides provided for experimental use sent to Dr. Stephen Robbins, University of Calgary, Calgary, Canada, Oct. 21, 1996.
Che-Hong Chen, List of peptides provided for experimental use sent to Dr. Patricia Hinkle, University of Rochester Medical School, Rochester, New York, U.S., Oct. 21, 1996.
Che-Hong Chen, List of peptides provided for experimental use sent to Dr. Susan Sergeant, Bowman Gray School of Medicine, Winston Salem, North Carolina, U.S., Oct. 21, 1996.
Che-Hong Chen, List of peptides provided for experimental use sent to Dr. Mohamed Boutjdir, VA Medical Center, Brooklyn, New York, U.S., Oct. 30, 1996.
John A. Johnson, List of peptides provided for experimental use sent to Drs. Willi;un Karnes and/or Shaun Weller, Mayo Foundation, SW Rochester, Minnesota, U.S. Dec. 16, 1996.
Che-Hong Chen, List of peptides provided for experimental use sent to Dr. David L. Greenen, Albert Einstein College of Medicine, Bronx, New York, U.S., Jan. 29, 1997.
Che-Hong Chen, List of peptides provided for experimental use sent to Dr. Judith Maloney, University of Pennsylvania School of Medicine, Philadelphia, Pennsylvania, U.S., Feb. 4, 1997.

(Continued)

*Primary Examiner* — David Lukton
(74) *Attorney, Agent, or Firm* — McDermott Will & Emery LLP

(57) ABSTRACT

The disclosed invention relates to methods of modifying peptide compositions to increase stability and delivery efficiency. Specifically, the disclosed invention relates to methods to increase the stability and delivery efficiency of protein kinase C (PKC) modulatory peptide compositions. A "therapeutic peptide composition" comprises a "carrier peptide" and a "cargo peptide." A "carrier peptide" is a peptide or amino acid sequence within a peptide that facilitates the cellular uptake of the therapeutic peptide composition. The "cargo peptide" is a PKC modulatory peptide. Peptide modifications to either the carrier peptide, the cargo peptide, or both, which are described herein increase the stability and delivery efficiency of therapeutic peptide compositions by reducing disulfide bond exchange, physical stability, reducing proteolytic degradation, and increasing efficiency of cellular uptake.

2 Claims, 20 Drawing Sheets

(56) References Cited

OTHER PUBLICATIONS

List of peptides provided for experimental use sent to Dr. Lobby on Feb. 25, 1997.

Che-Hong Chen, List of peptides provided for experimental use and related correspondence sent to and from Dr. Kevin Claffey, Beth Israel Deaconess Medical Center, Boston, Massachusetts, U.S., Jun. 2, 1997.

Che-Hong Chen, List of peptides provided for experimental use sent to Dr. Piero Biancani, East Greenwich, Rhode Island, U.S., Jun. 2, 1997.

Kevin P. Clafferty, Letter discussing peptides and related search results sent to Dr. Daria Mochly-Rosen, Stanford University School of Medicine, Stanford, California, U.S., Apr. 15, 1997.

John A. Johnson, List of peptides provided. for experimental use and related correspondence sent to and from Dr. Stuart: D. Critz, University of South Alabama College of Medicine, Mobile, Alabama, U.S., Jun. 3, 1997.

Che-Hong Chen, List of pep tides provided for experimental use and related journal article (Miyagawa el al.) sent to Dr. R. Kent Hermsmeyer, Oregon Regional Primate Research Center, Beavelton, Oregon, U.S., Jan. 5, 1998.

List of peptides provided for experimental use sent to Dr. Lobo, University of California, San Francisco, San Francisco, California, U.S., Feb. 11, 1998.

Che-Hong Chen, List of peptides provided for experimental use sent to Dr. Sailen Barik, University of Southern Alabama, Mobile, Alabama, U.S., Mar. 19, 1998.

Che-Hong Chen, List of peptides provided for experimental use and related correspondence sent to and from Dr. Richard Olsen, University of California, Los Angeles, School of Medicine, Los Angeles, California, U.S., Jul. 6, 1998.

Che-Hong Chen, List of peptides provided for experimental use and related correspondence sent to and from Dr. Susie Mihailidou, Royal North Shore Hospital, st. Leonards, Australia, Dec. 1, 1998.

Che-Hong Chen, List of peptides provided for experimental use and related correspondence sent to and from Dr. Jeffery Knauf, University of Cincinnati, Cincinnati, Ohio, U.S., Jul. 13, 1999.

Kevin P. Claffey, e-mail correspondence regarding peptides sent to Dr. Che-Hong Chen. Jun. 2, 1997.

Che-Hong Chen, List of peptides provided for experimental use sent to Dr. Richard A. Clark, State University of New York, Stony Brook, Stony Brook, New York, U.S., Jun. 2, 1997.

Richard A. Clark, e-mail correspondence regarding peptides sent to and from Dr. Daria Mochly-Rosen, Jun. 2, 1997.

Che-Hong Chen, List of peptides provided for experimental use and related correspondence sent to and from Dr. Susie Mihailidou, Royal North Shore Hospital, St. Leonards, Australia, Jul. 13, 1998.

Che-Hong Chen, List of peptides provided for experimental use sent to Dr. Mohamed Boutjdir. VA Medical Center, Brooklyn, New York, U.S., Aug. 14, 1998.

Che-Hong Chen, List of pep tides provided for experimental use sent to Dr. John D. Levine, University of California, San Francisco, San Francisco, California, U.S. Mar. 10, 1999.

Daria Mochly-Rosen, Material Transfer Agreement and List of peptides provided for experimental use sent to Dr. John D. Levine, University of California, San Francisco, San Francisco, California, U.S. Feb. 25, 1999.

Che-Hong Chen, List of peptides provided for experimental use sent to Dr. Steve Black, University of California. San Francisco, San Francisco, California, U.S., Jan. 5, 1998.

Che-Hong Chen, List of peptides provided for experimental use sent to Dr. Derek Miles Yellon, Hatter Institute for Cardiovascular Studies, University of College Hospital and Medical School, London, England. United Kingdom, Jun. 25, 1998.

Che-Hong Chen, List of peptides provided for experimental use sent to Dr. Katherine Murray, Vanderbilt University School of Medicine, Nashville, Tennessee, U.S., Sep. 8, 1998.

Che-Hong Chen, List of peptides provided for experimental use sent to Dr. Adrienne Gordon, University of California, San Francisco, San Francisco, California, U.S., Sep. 10, 1998.

Che-Hong Chen, List of peptides provided for experimental use sent to Dr. W. Barry VanWinkle, University of Texas Medical School at Houston, Houston, Texas, U.S. Sep. 28, 1995.

Che-Hong Chen, List of peptides provided for experimental use and related correspondence sent to and from Dr. Derek Miles Yellon, Hatter Institute for Cardiovascular Studies. University of College Hospital and Medical School, London, England, United Kingdom, Oct. 14, 1998.

Che-Hong Chen, List of pep tides provided for experimental use and related correspondence regarding peptides project outline sent to and from Dr. Fiorenzo Battaini, University of Milano. Milano. Italy, Oct. 15, 1998.

Che-Hong Chen, List of peptides provided for experimental use and related correpondence sent to and from Dr. Yasuki Kihara, Kyoto University, Kyoto, Japan, Oct. 15, 1998.

Che-Hong Chen, List of peptides provided for experimental use and related correspondence sent to and from Dr. Naoaki Saito, Kobe University, Kobe, Japan, Oct. 15, 1998.

Che-Hong Chen, List of peptides provided for experimental use and related correspondence sent to and from Dr. Ashwani Malhotra, New York Medical College, Valhalla, New York, U.S., Oct. 16, 1998.

Daria Mochly-Rosen, Material Transfer Agreement and List of peptides provided for experimental use sent to Dr. Steve Black, University of California, San Francisco, San Francisco, California, U.S., Sep. 3, 1998.

Che-Hong Chen, List of peptides provided for experimental use and related correspondence sent to and from Dr. Allan Basbaum, W.M. Keck Foundation Center for Integrative Neuroscience, San Francisco, California, U.S., Oct. 21, 1998.

Che-Hong Chen, List of peptides provided for experimental use sent to Drs. Rik Derynck and Huizhou Fan, University of California, San Francisco, San Francisco, California. U.S., Oct. 27, 1998.

Che-Hong Chen, List of peptides provided for experimental use and related correspondence sent to and from Dr. Elissavet Kardami, University of Manitoba, Manitoba, Canada, Nov. 18, 1998.

Che-Hong Chen, List of peptides provided for experimental use and related correspondence sent to and from Dr. Guang S. Liu, University of South Alabama, Mobile, Alabama, U.S., Nov. 23, 1998.

Che-Hong Chen, List of peptides provided for experimental use sent to Dr. John Hayslett, Yale School of Medicine, New Haven, Connecticut, U.S., Dec. 14, 1998.

Daria Mochly-Rosen, Material Transfer Agreement and List of peptides provided for experimental use sent to Dr. Arshad Rahman, University of Illinois, Chicago, Illinois, U.S. Dec. 15, 1998.

Daria Mochly-Rosen, List of peptides provided for experimental use sent to Andrew P. Bradford, faxed on Dec. 18, 1998.

Daria Mochly-Rosen, Material Transfer Aggreement sent to Dr. Yuri Volkov, Trinity Centre for Health Sciences, St. James's Hospital, Dublin. Ireland, Dec. 15, 1998.

Daria Mochly-Rosen, Material Transfer Agreement and related document sent to Dr. Tish Murphy, NIEHS, NIH, Research Triangle Park, North Carolina. U.S. Dec. 15, 1998.

Che-Hong Chen, List of peptides provided for experimental use sent to Dr. Babu Padanilam, Washington University Medical School, St. Louis, Missouri, U.S., Jan. 5, 1999.

Daria Mochly-Rosen, Material Transfer Agreement and List of peptides provided for experimental use sent to Dr. Eric J. Nelson, University of Colorado, Denver, Colorado, U.S., Jan. 14, 1999.

Che-Hong Chen, List of peptides provided for experimental use sent to Dr. Hyeon-Gyu Shin, Vanderbilt University School of Medicine, Nashville, Tennessee, U.S., Jan. 20, 1999.

Daria Mochly-Rosen, Material Transfer Agreement, List of peptides provided for experimental use and related correspondence sent to and from Dr. Mita Das, University of Colorado Health Sciences Center, Denver, Colorado, U.S., Jan. 11, 1999.

Che-Hong Chen, List of peptides provided for experimental use and related correspondence sent to and from Dr. Rafuel Nesher, Hebrew University-Hadassah Medical Center, Jerusalem, Israel, Feb. 10, 1999.

Daria Mochly-Rosen. Material Transfer Agreement, List of peptides provided for experimental use, and related correspondence sent to and from Dr. Steven Pelech, University of British Columbia, British Columbia, Canada, Feb. 10, 1999.

(56) References Cited

OTHER PUBLICATIONS

Che-Hong Chen, List of peptides provided for experimental use and related correspondence sent to and from Dr. Naoaki Saito, Kobe University, Kobe, Japan, Feb. 10, 1999.
Che-Hong Chen, List of peptides provided for experimental use sent to Dr. Umberto Kucich; School of Dental Medicine, Philadelphia, Pennsylvania, U.S., Mar. 11, 1999.
List of peptides provided for experimental use sent to Dr. Imogen Coe, York University, Ontario, Canada, Apr. 8, 1999.
Che-Hong Chen, List of peptides provided for experimental use and related correspondence sent to and from Dr. Mireia Gomez-Angelats, Research Triangle Park, North Carolina, U.S. Jul. 13, 1999.
Daria Mochly-Rosen, Material Transfer Agreement, List of peptides provided for experimental use, and related correspondence sent to and from Dr. Jau-Shyong Hong, NIEHS, NIH, Research Triangle Park, North Carolina, U.S., Jul. 13, 1999.
Che-Hong Chen, List of peptides provided for experimental use and related correspondence sent to Dr. Anne-Marie Schmitt-Verhulst, Centre d'Immunologie INSERM-CNRS de Marseille-Luminy, Marseilles, France, Jul. 14, 1999.
Daria Mochly-Rosen, Material Transfer Agreement and List of peptides provided for experimental use sent to Dr. John D. Roberts, NIEHS, NIH, Research Triangle Park, North Carolina. U.S., Jul. 14, 1999.
Che-Hong Chen, List of peptides provided for experimental use sent to Dr, Jeffery Knauf, University of Cincinnati, Cincinnati, Ohio, U.S. Aug. 10, 1999.
Daria Mochly-Rosen, Material Transfer Agreement sent to Dr. Johannes W. Hell , University of Wisconsin Medical School, Madison, Wisconsin, U.S. Sep. 22, 1999.
Che-Hong Chen, List of peptides provided for experimental use and related correspondence sent to and from Dr. Eric Nelson, University of Colorado, Denver, Colorado, U.S. Oct. 2, 1999.
Che-Hong Chen, Material Transfer Agreement, List of peptides provided for experimental use, and related correspondence sent to and from Dr. Yukitaka Shizukuda, University of Illinois, Chicago, Illinois, U.S. Nov. 5, 1999.
Daria Mochly-Rosen, Material Transfer Agreement sent to Dr. Hesam Dehghani, University of Guelph, Ontario, Canada, Nov. 8, 1999.
Joan Brugge for Dr. Cindy Miranti , Harvard Medical School, Boston, Massachusetts, U.S., Material Transfer Agreement and related correspondence sent to and from Dr. Daria Mochly-Rosen, Dec. 21, 1999.
Daria Mochly-Rosen, Material Transfer Agreement and List of peptides provided for experimental use and related correspondence sent to and from Dr. Alexei Kourakine, Buck Center, San Franciso, California, U.S., Jan. 7, 2000.
Daria Mochly-Rosen, Material Transfer Agreement, List of peptides provided for experimental use and related correspondence sent to and from Dr. Ti-Zhi Su, Parke-Davis, Ann Arbor, Michigan. U.S., Jan. 28, 2000.
Daria Mochly-Rosen, Material Transfer Agreement and List of peptides provided for experimental use sent to Dr. Clive Baumgarten, Virginia Commonwealth University, Richmond, Virginia, U. S., Feb. 3, 2000.
Che-Hong Chen, List of peptides provided for experimental use and related correspondence sent to and from Dr. Fiorenzo Battaini, University of Milano, Milano, Italy, Nov. 2. 1998.
Daria Mochly-Rosen, Material Transfer Agreement and List of peptides provided for experimental use sent to Dr, Pedro A. Jose, Georgetown University Hospital , Washington, DC. U.S., Feb. 17, 1999.
Che-Hong Chen, List of peptides provided for experimental use sent to Dr. Karen M. Ridge, Northwestern University, Chicago, Illinois, U.S., Apr. 4, 2000.
Aizawa et al., "Protein kinase C-epsilon primes the cardiac sarcolemmal adenosine triphosphate-sensitive potassium channel to modulation by isoflurane", Anesthesiology, vol. 101, No. 2, pp. 381-389 (2004).

Alessandri-Haber et al., "A transient receptor potential vanilloid 4-dependent mechanism of hyperalgesia is engaged by concerted action of inflammatory mediators", J. Neurosci., vol. 26, No. 14, pp. 3864-3874 (2006).
Aley and Levine, "Contribution of 5- and 12-lipoxygenase products to mechanical hyperalgesia induced by prostaglandin E(2) and epinephrine in the rat", Exp. Brain Res., vol. 148, No. 4, pp. 482-487 (2003).
Aley et al. "Chronic hypersensitivity for inflanunatory nociceptor sensitization mediated by the epsilon isozyme of protein kinase c", J. Neurosci., vol. 20, No. 12, pp. 4680-4685 (2000).
Alvarez et al., "Molecular basis for angiotensin II-induced increase of chloride/bicarbonate exchange in the myocardium", Circ. Res., vol. 89, No. 12, pp. 1246-1253 (2001).
Amadesi et al., "Protease-activated receptor 2 sensitizes TRPV1 by protein kinase Cepsilon- and A-dependent mechanisms in rats and mice", J. Physiol., vol. 575, No. 2, pp. 555-571 (2006).
Andrukhiv et al., "Opening mitoKATP increases superoxide generation from complex I of the electron transport chain", Am. J. Physiol. Heart Circ. Physiol., vol. 291, pp. H2067-H2074 (2006).
Banci et al., "Molecular dynamics characterization of the C2 domain of protein kinase Cbeta", J. Bioi. Chem., vol. 277, No. 15, pp. 12988-12997 (2002).
Baroudi et al., "Protein kinase C activation inhibits Cav1.3 calcium channel at NH2-terminal serine 81 phosphorylation site", Am. J. Physiol. Heart Circ. Physiol., Vaol. 291, pp. H1614-H1622 (2006).
Basu et al., "Phosphorylation of a UDP-glucuronosyltransferase regulates substrate specificity", PNAS USA, vol. 102, No. 18, pp. 6285-6290 (2005).
Begley et al., "Biodistribution of intracellularly acting peptides conjugated reversibly to tat", Biochem. Biophys. Res. Commun., vol. 318, No. 4, p. 949-954 (2004).
Berna et al., "CCK causes PKD1 activation in pancreatic acini by signaling through PKC-delta and PKC-independent pathways", Biochim. Biophys. Acta, vol. 1773, No. 4, pp. 483-501 (2007).
Besena et al., "Activation of protein kinase C epsilon inhibits the two-pore domain K+ channel, TASK-1, inducing repolarization abnormalities in cardiac ventricular myocytes", J. Biol. Chem., vol. 279, No. 32, pp. 33154-33160 (2004).
Brandman et al., "Peptides derived from the C2 domain of protein kinase C epsilon (epsilon PKC) modulate epsilon PKC activity and identify potential protein-protein interaction surfaces", J. Biol. Chem., vol. 282, No. 6, pp. 4113-4123 (2007).
Braun and Mochly-Rosen, "Opposing effects of delta- and zeta-protein kinase C isozymes on cardiac fibroblast proliferation: Use of isozyme-selective inhibitors", J. Mol. Cell Cardiol., vol. 35, No. 8, p. 895-903 (2003).
Bright et al., "Protein kinase C delta mediates cerebral reperfusion injury in vivo", J. Neuroscience, vol. 24, No. 31, p. 6880-6888 (2004).
Bright and Mochly-Rosen, "The role of protein kinase C in cerebral ischemic snd reperfusion in injury", Stroke, vol. 36, No. 12, p. 2781-2790 (2005).
Brunelli et al., "Beta catenin-independent activation of MyoD in presomitic mesoderm requires PKC and depends on Pax3 transcriptional activity", Dev. Biol., vol. 304, No. 2, pp. 604-614 (2007).
Brzoska et al., "The product of the ataxiatelangiectasia group D complementing gene, ATDC, interacts with a protein kinase C substrate and inhibitor", Proc. Natl. Acad. Sci. USA, vol. 92, No. 17, pp. 7824-7828 (1995).
Budas et al., "Mitochondrial protein kinase Cepsilon (PKCepsilon): emerging role in cardiac protection from ischaemic damage", Biochem. Soc. Trans., vol. 35, Pt. 5, No. 1052-1054 (2007).
Budas et al., "Competitive inhibitors and allosteric activators of protein kinase C isoenzymes: a personal account and progress report on transferring academic discoveries to the clinic", Biochem. Soc. Trans., vol. 35, Pt. 5, No. 1021-1026 (2007).
Budas et al., "Cardioprotective mechanisms of PKC isozyme-selective activators and inhibitors in the treatment of ischemia-reperfusion injury", Pharmacol. Res., vol. 55, No. 6, pp. 523-536 (2007).
Buhagiar et al., "Protein kinase Cepsilon contributes to regulation of the sarcolemmal Na(+)-K(+) pump", Am. J. Physiol. Cell Physiol., vol. 281, No. 3, pp. C1059-C1063 (2001).

(56) References Cited

OTHER PUBLICATIONS

Cardone et al., "Phorbol myristate acetate-mediated stimulation of trancytosis and apical recycling in MDCK cells", J. Cell. Biol., vol. 124, No. 5, p. 717-727 (1994).
Cardone et al., "Signal transduction by the polymeric immunoglobulin receptor suggests a role in regulation of receptor transcytosis", J. Cell. Biol., vol. 133, No. 5, p. 997-1005 (1996).
Cesare et al., "Specific involvement of PKC-epsilon in sensitization of the neuronal response to painful heat", Neuron, vol. 23, No. 3, pp. 617-624 (1999).
Chang and Tepperman "Effects of selective PKC isoform activation and inhibition on TNF-α-induced injury and apoptosis in human intestinal epithelial cells", British Journal of Pharmacology, vol. 140, pp. 41-52 (2003).
Chang et al., "The role of protein kinase C isozymes in TNF-alpha-induced cytotoxicity to a rat intestinal epithelial cell line", Am. J. Physiol. Gastrointest. Liver Physiol., vol. 280, No. 4, pp. G572-G583 (2001).
Chaudary et al., "The adenosine transporter, mENT1, is a target for adenosine receptor signaling and protein kinase Cepsilon in hypoxic and pharmacological preconditioning in the mouse cardiomyocyte cell line, HL-1", J. Pharmacol. Exp. Ther., vol. 310, No. 3, pp. 1190-1198 (2004).
Chen et al., "Molecular transporters for peptides: delivery of cardioprotective εPKC agonist peptide into cells and intact ischemic heart using a transport system, $R_7$", Chem. Biol., vol. 140, pp. 1-7 (2001).
Chen et al., "Opposing effects of delta and xi PKC in ethanol-induced cardioprotection", J. Mol. Cell. Cardiol., vol. 33, pp. 581-585 (2001).
Chen et al., "Opposing cardioprotective actions and parallel hypertrophic effects of delta PKC and epsilon PKC", PNAS, vol. 98, No. 20, p. 11114-11119 (2001).
Chen et al., "Specific modulation of Na+ channels in hippocampal neurons by protein kinase C epsilon," J. Neurosci., vol. 25, No. 2, pp. 507-513 (2005).
Chen et al., "Cardioprotection from ischemia by a brief exposure to physiological levels of ethanol: role of epsilon protein kinase c", Proc. Natl. Acad. Sci. USA, vol. 96, No. 22, pp. 12784-12789 (1999).
Chie et al., "Oncogenic and activated wild-type ras-p21 proteins induce different isoforms of protein kinase C in mitogenic signal transduction", J. Protein. Chem., vol. 22, No. 7-8, pp. 625-629 (2003).
Churchill et al., "Reperfusion-induced translocation of deltaPKC to cardiac mitochondria prevents pyruvate dehydrogenase reactivation", Circ. Res., vol. 97, No. 1, pp. 79-85 (2005).
Claro et al., "Alpha- and epsilon-protein kinase C activity during smooth muscle cell apoptosis in response to gamma-radiation", J. Pharmacol. Exp. Ther., vol. 322, No. 3, pp. 964-972 (2007).
Cosen-Binker et al., "Alcohol/cholecystokinin-evoked pancreatic acinar basolateral exocytosis is mediated by protein kinase C alpha phosphorylation of Munc18c", Biol. Chem., vol. 282, No. 17, pp. 13047-13058 (2007).
Costa et al., "cGMP signaling in pre- and post-conditioning: the role of mitochondria", Cardiovasc. Res., vol. 77, No. 2, 99. 344-352 (2008).
Costa et al., "Protein kinase G transmits the cardioprotective signal from cytosol to mitochondria", Circ. Res., vol. 97, pp. 329-336 (2005).
Csukai et al., "Molecular genetic approaches. II. Expression-interaction cloning", Methods Mol. Bioi., vol. 88, pp. 133-139 (1998).
Csukai and Mochly-Rosen, "Pharmacologic modulation of protein kinase C isozymes: The role of RACKs and subcellular localization", Pharmacological Research, vol. 39, No. 4, pp. 253-259 (1999).
Csukai et al., "The coatomer protein beta'COP, a selective binding protein (RACK) for protein kinase Cepsilon", J. Biol. Chem., vol. 272, No. 46, pp. 29200-29206 (1997).
Dallas et al., "Ca2+ antagonist-insensitive coronary smooth muscle contraction involves activation of epsilon-protein kinase C-dependent pathway", Am. J. Physiol. Cell Physiol., vol. 285, No. 6, pp. C1454-C1463 (2003).

De et al., "Role of protein kinase C in control of ethanol-modulated beta-endorphin release from hypothalamic neurons in primary cultures", J. Pharmacol. Exp. Ther., vol. 301, No. 1, pp. 119-128 (2002).
Dehgani et al., "Subcellular localization of protein kinase C delta and epsilon affects transcriptional and post-transcriptional processes in four-cell mouse embryos", Reproduction, vol. 130, No. 4, pp. 453-465 (2005).
Dell et al., "The betagamma subunit of heterotrimeric G proteins interacts with RACKI and two other WD repeat proteins", J. Bioi. Chem., vol. 277, No. 51, pp. 49888-49895 (2002).
Dempsey et al., "Protein kinase C isozymes and the regulation of diverse cell responses", Am. J. Physiol. Lung Cell Mol. Physiol., vol. 279, No. 3, pp. L429-L438 (2000).
Dey et al., "Fatty acid represses insulin receptor gene expression by impairing HMGA1 through protein kinase Cepsilon", Biochem. Biophys. Res. Commun., vol. 357, pp. 474-479 (2007).
Diamond et al., (1991). "The role of adenosine and adenosine transport in ethanol-induced cellular tolerance and dependence. Possible biologic and genetic markers of alcoholism", Ann. N. Y. Acad. Sci., vol. 625, pp. 473-487 (1991).
Dina, et al., "Primary afferent second messenger cascades interact with specific integrin subunits in producing inflammatory hyperalgesia", Pain, vol. 115, No. 1-2, pp. 191-203 (2005).
Disatnik, et al., "Phospholipase C-gamma 1 binding to intracellular receptors for activated protein kinase C", PNAS, vol. 91, No. 2, p. 559-563 (1994).
Disatnik, et al., "Distinct responses of protein kinase C Isozymes to c-erbB-2 activation in SKBR-3 human breast carcinoma cells", Cell Growth Differ., vol. 5, No. 8, p. 873-880 (1994).
Disatnik et al., "Localization of protein kinase C isozymes in cardiac myocytes", Exp. Cell Res., vol. 210, No. 2, pp. 287-297 (1994).
Disatnik et al., "Sequential activation of individual PKC isozymes in integrin-mediated muscle cell spreading: A role of MARCKS in an integrin signaling pathway", J. Cell Science, vol. 115, pp. 2151-2163 (2002).
Disatnik et al., (1995). "Stimulus-dependent subcellular localization of activated protein kinase C; a study with acidic fibroblast growth factor and transforming growth factor-beta 1 in cardiac myocytes", J. Mol. Cell Cardiol., vol. 27, pp. 2473-2481 (1995).
Dorn et al., "Intracellular transport mechanisms of signal transducers", Annu. Rev. Physiol., vol. 64, pp. 407-429 (2002).
Dorn et al., (1999). "Sustained in vivo cardiac protection by a rationally designed peptide that causes epsilon protein kinase C translocation", Proc. Natl. Acad. Sci. USA, vol. 96, No. 22, pp. 12798-12803 (1999).
Du et al., "Selective regulation of IL-10 signaling and function by zymosan", J. Immunol., vol. 176, No. 8, pp. 4785-4792 (2006).
Endemann et al., "Methods for detecting binding proteins: an introduction", Methods Mol. Biol., vol. 233, pp. 307-325 (2003).
Endemann et al., "Cytotoxicity of pEGFP vector is due to residues encoded by multiple cloning site", Anal. Biochem., vol. 313, pp. 345-347 (2003).
Fanning et al., "CD44 cross-linking induces protein kinase C-regulated migration of human T lymphocytes", Int. Immunol., vol. 17, No. 4, pp. 449-458 (2005).
Felber et al., "Inhibition of novel protein kinase C-epsilon augments TRAIL-induced cell death in A549 lung cancer cells", Pathol. Oncol. Res., vol. 13, No. 4, pp. 295-301 (2007).
Flescher et al., "Protein kinase C epsilon mediates the induction of P-glycoprotein in LNCaP prostate carcinoma cells", Cell Signal, vol. 14, pp. 37-43 (2002).
Gao et al., "Activation of alpha1B-adrenoceptors alleviates ischemia/reperfusion injury by limitation of mitochondrial Ca2+ overload in cardiomyocytes", Cardiovasc. Res., vol. 75, No. 3, pp. 584-595 (2007).
Gao et al., "Resistin, an adipocytokine, offers protection against acute myocardial infarction", J. Mol. Cell Cardiol., vol. 43, No. 5, pp. 601-609 (2007).
Garcia-Navarro et al., "Developmental expression of protein kinase C subspecies in rat brain-pituitary axis", Mol. Cell Endocrinol., vol. 103, No. 1-2, pp. 133-138 (1994).

(56) References Cited

OTHER PUBLICATIONS

Garg et al., "Protein kinase C isoform-dependent modulation of ATP-sensitive K+ channels in mitochondrial inner membrane", AM. J. Physiol. Heart Circ. Physiol., vol. 293, pp. H322-H332 (2007).
Ghosh et al., "Role of protein kinase C in arginine vasopressin-stimulated ERK and p70S6 kinase phosphorylation", J. Cell. Biochem., vol. 91, No. 6, pp. 1109-1129 (2004).
Gray et al., "A selective epsilon-protein kinase C antagonist inhibits protection of cardiac myocytes from hypoxia-induced cell death", J. Biol. Chem., vol. 272, No. 49, pp. 30945-30951 (1997).
Gray, et al., "Preservation of base-line hemodynamic function and loss of inducible cardioprotection in adult mice lacking protein kinase C epsilon", J. Biol. Chem., vol. 279, No. 5, p. 3596-3604 (2004).
Graeler et al., "Protein kinase C epsilon dependence of the recovery from down-regulation of S1P1 G protein-coupled receptors of T lymphocytes", J. Biol. Chem., vol. 278, No. 30, pp. 27737-27741 (2003).
Gregory, et al., "Increased particulate partitioning of PKC epsilon reverses susceptibility of phospholamban knockout hearts to ischemic injury", J. Mol. Cell Cardiol., vol. 36, No. 2, pp. 313-318 (2004).
Hassouna et al., "PKC-epsilon is upstream and PKC-alpha is downstream of mitoKATP channels in the signal transduction pathway of ischemic preconditioning of human myocardium", Am. J. Physiol. Cell Physiol., vol. 287, pp. C1418-C1425 (2004).
Hayabuchi et al., "Angiotensin II inhibits and alters kinetics of voltage-gated K(+) channels of rat arterial smooth muscle", Am. J. Physiol. Heart Circ. Physiol., vol. 281, No. 16, pp. H2480-H2489 (2001).
Hayabuchi et al., "Angiotensin II inhibits rat arterial KATP channels by inhibiting steady-state protein kinase A activity and activating protein kinase Cε", J. Physiol. vol. 530, Pt. 2, pp. 193-205 (2001).
Heider et al., "PAR1-type thrombin receptor stimulates migration and matrix adhesion of human colon carcinoma cells by a PKCepsilon-dependent mechanism", Oncol. Res., vol. 14, No. 10, pp. 475-482 (2004).
Hodge et al., "Supersensitivity to allosteric GABA(A) receptor modulators and alcohol in mice lacking PKCepsilon", Nat. Neurosci., vol. 2, No. 11, pp. 997-1002 (1999).
Hool "Protein kinase C isozyme selective peptides—A current view of what they tell us about location and function of isozymes in the heart", Current Pharmaceutical Design, vol. 11, pp. 549-559 (2005).
Hool "Hypoxia increases the sensitivity of the L-type Ca(2+) current to beta-adrenergic receptor stimulation via a C2 region-containing protein kinase C isoform", Circ. Res., vol. 87, No. 12, pp. 1164-1171 (2000).
Hool "Differential regulation of the slow and rapid components of guinea-pig cardiac delayed rectifier K+ channels by hypoxia," J. Physiol., vol. 554(pt. 3), 743-754 (2004).
Hu et al., "Evidence for functional role of epsilonPKC isozyme in the regulation of cardiac Ca(2+) channels", Am. J. Physiol. Heart. Circ. Physiol., vol. 279 No. 6, pp. H2658-h2664 (2000).
Huang et al., "Myofilament anchoring of protein kinase C-epsilon in cardiac myocytes", J. Cell. Sci., vol. 117, Pt. 10, pp. 1971-1978 (2004).
Huang et al., "Mechanism of oleic acid-induced gap junctional disassembly in rat cardiomyocytes", J. Mol. Cell CArdiol., vol. 37, No. 3, pp. 755-766 (2004).
Hucho et al., "Estrogen controls PKCε-dependent mechanical hyperalgesia through direct action on nociceptive neurons", Euro. J. Neurosci., vol. 24, No. 2, pp. 527-534 (2006).
Hudecz et al., "Medium-sized peptides as built in carriers for biologically active compounds", Med. Res. Rev., vol. 25, No. 6, pp. 679-736 (2005).
Hundle et al., "An inhibitory fragment derived from protein kinase Cepsilon prevents enhancement of nerve growth factor responses by ethanol and phorbol esters", J. Biol. Chem., vol. 272, No. 23, p. 15028-15035 (1997).
Ikeno et al., "Impaired perfusion after myocardial infarction is due to reperfusion-induced deltaPKC-mediated myocardial damage", Cardiovasc. Res., vol. 73, No. 4, pp. 699-709 (2007).
Inagaki and Mochly-Rosen, "DeltaPKC-mediated activation of epsilonPKC in ethanol-induced cardiac protection from ischemia", J. Mol. Cell Cardiol., vol. 39, No. 2, pp. 203-211 (2005).
Inagaki et al., "Tissue angiotensin during progression of ventricular hypertrophy to heart failure in hypertensive rats; differential effects on PKCε and PKCβ", J. Mol. Cell Cardiol., pp. 1-9 (2002).
Inagaki et al., "Epsilon protein kinase C as a potential therapeutic target for the ischemic heart", Cardiovasc. Res., vol. 70, No. 2, pp. 222-230 (2006).
Inagaki et al., "Cardioprotection by epsilon-protein kinase C activation from ischemia: Continuous delivery and antiarrythmic effect of an epsilon-protein kinase C-activating peptide", Circulation, vol. 111, No. 1, pp. 44-50 (2005).
Inagaki et al., "Additive protection of the ischemic heart ex vivo by combined treatment with delta-protein kinase C inhibitor and epsilon-protein kinase C activator", Circulation, vol. 108, p. 869-875 (2003).
Inagaki et al., "Inhibition of delta-protein kinase C protects against reperfusion injury of the ischemic heart in vivo", Circulation vol. 108, No. 19, p. 2304-2307 (2003).
Inagaki et al., "Anti-ischemic effect of a novel cardioprotective agent, JTV519, is mediated through specific activation of delta-isoform of protein kinase C in rat ventricular myocardium", Circulation, vol. 101, No. 7, pp. 797-804 (2000).
International Search Report for PCT Patent Application No. PCT/US2008/051706 mailed Sep. 24, 2008, Application published as International Patent Publication No. WO 2008/089491 A2 on Jul. 24, 2008.
Jaburek et al., "Mitochondrial PKC epsilon and mitochondrial ATP-sensitive K+ channel copurify and coreconstitute to form a functioning signaling module in proteoliposomes", Circ Res., vol. 99, pp. 878-883 (2006).
Jin et al., "Cardioprotection mediated by sphingosine-1-phosphate and ganglioside GM-1 in wild-type and PKC epsilon knockout mouse hearts", Am. J. Physiol. Heart Circ Physiol., vol. 282, No. 6, p. H1970-H1977 (2002).
Johnson and Mochly-Rosen, "Inhibition of the spontaneous rate of contraction of neonatal cardiac myocytes by protein kinase C isozymes. A putative role for the epsilon isozyme", Circ. Res., vol. 76, No. 4, pp. 654-663 (1995).
Johnson et al., "Prolonged phorbol ester treatment down-regulates protein kinase C isozymes and increases contraction rate in neonatal cardiac myocytes", Life Sci., vol. 57, No. 11, p. 1027-1038 (1995).
Johnson et al., "A protein kinase C translocation inhibitor as an isozyme-selective antagonist of cardiac function", J. Biol. Chem., vol. 271, No. 40, p. 24962-24966 (1996).
Johnson et al., "An improved permeabilization protocol for the introduction of peptides into cardiac myocytes. Application to protein kinase C research", Circ. Res., vol. 79, No. 6, pp. 1086-1099 (1996).
Jones et al., "Modulation of LPS stimulated NF-kappaB mediated nitric oxide production by PKC-epsilon and JAK2 in RAW macrophages", J. Inflamm., vol. 4, pp. 23 9 pgs. (2007).
Joseph et al., "PLC-beta 3 signals upstream of PKC epsilon in acute and chronic inflammatory hyperalgesia", Pain, 132, No. 1-2, pp. 67-73 (2007).
Joseph et al., "Hyperalgesic priming in the rat demonstrates marked sexual dimorphism", Pain, vol. 105, No. 1-2, pp. 143-150 (2003).
Jung et al., "Activation of protein kinase C-delta attenuates kainate-induced cell death of cortical neurons", Neuroreport, vol. 16, No. 7, pp. 741-744 (2005).
Jung et al., "Role for PKC-epsilon in neuronal death induced by oxidative stress", Biochem. Biophys. Res. Commun., vol. 320, No. 3, pp. 789-794 (2004).
Kanno et al., "The linoleic acid derivative DCP-LA selectively activates PKC-epsilon, possibly binding to the phosphatidylserine binding site", J. Lipid. Res., vol. 47, No. 6, pp. 1146-1156 (2006).
Karliner et al., "Neonatal mouse cardiac myocytes exhibit cardioprotection induced by hypoxic and pharmacologic precondi-

(56) References Cited

OTHER PUBLICATIONS tioning and by transgenic overexpression of human Cu/Zn superoxide dismutase", J. Mol. Cell Cardiol., vol. 32, No. 10, pp. 1779-1786 (2000).

Khasar et al., "Epinephrine produces a beta-adrenergic receptor-mediated mechanical hyperalgesia and in vitro sensitization of rat nociceptors", J. Neurophysiol. vol. 81, No. 3, pp. 1104-1112 (1999).

Khasar et al., "A novel nociceptor signaling pathway revealed in protein kinase C epsilon mutant mice", Nueron vol. 24, No. 1, pp. 253-260 (1999).

Kheifets et al., "Protein kinase C delta (deltaPKC)-annexin V interaction: a required step in deltaPKC translocation and function", J. Biol. Chem., vol. 281, No. 32, pp. 23218-23226 (2006).

Kim et al. "Isoform-specific induction of PKC-epsilon by high glucose protects heart-derived H9c2 cells against hypoxic injury", Biochem. Biophys. Res. Commun., vol. 309, No. 1, pp. 1-6 (2003).

Kim et al., "Role of PKC-delta during hypoxia in heart-derived H9c2 cells", Jpn. J. Physiol., vol. 54, No. 4, pp. 405-414 (2004).

Kim et al., "Ischemic preconditioning via epsilon protein kinase C activation requires cyclooxygenase-2 activation in vitro", Nueroscience, vol. 145 No. 3, pp. 931-941 (2007).

Kinsey et al., "Identification of calcium-independent phospholipase A2gamma in mitochondria and its role in mitochondrial oxidative stress", Am. J. Physiol. Renal Physiol., vol. 292, No. 2, pp. F853-F860 (2006).

Knauf et al., "Involvement of protein kinase Cepsilon (PKCepsilon) in thyroid cell death. A truncated chimeric PKCepsilon cloned from a thyroid cancer cell line protects thyroid cells from apoptosis", J. Biol. Chem., vol. 274, No. 33, p. 23414-23425 (1999).

Knauf et al., "Isozyme-specific abnormalities of PKC in thyroid cancer: Evidence for post-transcriptional changes in PKC epsilon", J. Clin. Endocrinol. Metab., vol. 85, No. 5, pp. 2150-2159 (2002).

Koon et al., "Substance P stimulates cyclooxygenase-2 and prostaglandin E2 expression through JAK-STAT activation in human colonic epithelial cells", J. Immunol., vol. 176, No. 8, pp. 5050-5059 (2006).

Koon et al., "Substance P-stimulated interleukin-8 expression in human colonic epithelial cells involves protein kinase Cdelta activation", J. Pharmacol. Exp. Ther., vol. 314, No. 3, pp. 1393-1400 (2005).

Koponen et al., "Prevention of NMDA-Induced death of cortical neurons by inhibition of protein kinase Czeta", J. Neurochem., vol. 86, No. 2, pp. 442-450 (2003).

Koyanagi et al., "Pharmacological inhibition of epsilon PKC suppresses chronic inflammation in murine cardiac transplantation model", J. Mol. Cell Cardiol., vol. 43, No. 4, pp. 517-522 (2007).

Lange-Asschenfeldt et al., "Epsilon protein kinase C mediated ischemic tolerance requires activation of the extracellular regulated kinase pathway in the organotypic hippocampal slice", J. Cereb. Blood Flow. Metab. vol. 24, No. 6, pp. 636-645 (2004).

Laudanna et al., "Evidence of zeta protein kinase C involvement in polymorphonuclear neutrophil integrin-dependent adhesion and chemotaxis", J. Biol. Chem., vol. 273, No. 46, pp. 30306-30315 (1998).

Lee et al., "Isozyme-specific inhibitors of protein kinase C translocation: effects on contractility of single permeabilized vascular muscle cells of the ferret", J. Physiol., vol. 517(Pt. 3), pp. 709-720 (1999).

Lee and Ro, "Peripheral metabotropic glutamate receptor 5 mediates mechanical hypersensitivity in craniofacial muscle via protein kinase C dependent mechanisms", Neurosci., vol. 146, No. 1, pp. 375-383 (2007).

Leinweber et al., "Regulation of protein kinase C by the cytoskeletal protein calponin", J. Biol. Chem., vol. 275, No. 51, pp. 40329-40336 (2000).

Li et al., "Protein kinase Cgamma mediates ethanol withdrawal hyper-responsiveness of NMDA receptor currents in spinal cord motor neurons", Br. J. Pharmacol., vol. 144, No. 3, pp. 301-307 (2005).

Lidington et al., "A role for proteinase-activated receptor 2 and PKC-epsilon in thrombin-mediated induction of decay-accelerating factor on human endothelial cells", Am. J. Physiol. Cell Physiol. vol. 286, No. 6, pp. C1437-C1447 (2005).

Liedtke et al., "Protein kinase C epsilon-dependent regulation of cystic fibrosis transmembrane regulator involves binding to a receptor for activated C kinase (RACK1) and RACK1 binding to Na+/H+ exchange regulatory factor", J. Biol. Chem., vol. 277, No. 25, pp. 22925-22933 (2002).

Liron et al., "Rational design of a selective antagonist of epsilon protein kinase C derived from the selective allosteric agonist, pseudo-RACK peptide", J. Mol. Cell Cardiol., vol. 42, No. 4, pp. 835-841 (2007).

Liu et al., "Protein kinase C-epsilon is responsible for the protection of the preconditioning in rabbit cardiomyocytes", J. Mol. Cell Cardiol., vol. 31, No. 10, p. 1937-1948 (1999).

Ludwig et al., "Protein kinase C translocation and Src protein tyrosine kinase activation mediate isoflurane-induced preconditioning in vivo: potential downstream targets of mitochondrial adenosine triphosphate-sensitive potassium channels and reactive oxygen species", Anesthesiology, vol. 100, No. 3, pp. 532-539 (2004).

Mackay and Mochly-Rosen, "An inhibitor of p38 mitogen-activated protein kinase protects neonatal cardiac myocytes from ischemia", J. Biol. Chem., vol. 274, No. 10, p. 6272-6279 (1999).

Mackay et al., "Arachidonic acid protects neonatal rat cardiac myocytes from ischaemic injury through epsilon protein kinase c", Cardiovasc. Res.,vol. 50, No. 1, pp. 65-74 (2001).

Mackay et al., "Involvement of a p38 mitogen-activated protein kinase phosphatase in protecting neonatal rat cardiac myocytes from ischemia", J. Mol. Cell Cardiol., vol. 32, No. 8, pp. 1585-1588 (2000).

Mackay et al., "Localization, anchoring, and functions of protein kinase C isozymes in the heart", J. Mol. Cell Cardiol., vol. 33, No. 7, pp. 1301-1307 (2001).

Malhotra et al., "PKC-{epsilon}-dependent survival signals in diabetic hearts", Am. J. Physiol. Heart Circ. Physiol., vol. 289, No. 4, pp. H1343-H1350 (2005).

Miller et al., "RACK1 regulates Src-mediated Sam68 and p190RhoGAP signaling", Oncogene, pp. 1-5 (2004).

Mamidipudi et al., "Peptide modulators of Src activity in G1 regulate entry into S phase and proliferation of NIH 3T3 cells", Biochem. Biophys. Res. Commun., vol. 352, No. 2, pp. 423-430 (2007).

Mangat et al., "Inhibition of phospholipase C-gamma 1 augments the decrease in cardiomyocyte viability by H2O2", Am. J. Physiol. Heart Circ. Physiol., vol. 291, No. 2, pp. H854-H860 (2006).

Marin et al., "Stimulation of oncogenic metabotropic glutamate receptor 1 in melanoma cells activates ERK1/2 via PKCepsilon", Cell Signal, vol. 18, No. 8, pp. 1279-1286 (2006).

Marinovic et al., "Preconditioning by isoflurane induces lasting sensitization of the cardiac sarcolemmal adenosine triphosphate-sensitive potassium channel mediated by a protein kinase C-delta-mediated mechanism", Anesthesiology, vol. 103, No. 3, pp. 540-547 (2005).

Mayne and Murray, et al., "Evidence that protein kinase Cepsilon mediates phorbol ester inhibition of calphostin C- and tumor necrosis factor-alpha-induced apoptosis in U937 histiocytic lymphoma cells", J. Biol. Chem., vol. 273, No. 37, pp. 24115-24121 (1998).

Mihailidou et al., "Rapid, nongenomic effects of aldosterone in the heart mediated by epsilon protein kinase C", Endocrinology, vol. 145, No. 2, pp. 773-780 (2004).

Miyamae et al., "Activation of epsilon protein kinase C correlates with a cardioprotective effect of regular ethanol consumption", Proc. Natl. Acad. Sci. USA, vol. 95, No. 14, pp. 8262-8267 (1998).

McNair et al., "Endothelin-1 promotes Ca2+ antagonist-insensitive coronary smooth muscle contraction via activation of epsilon-protein kinase C", Hypertension, vol. 43, No. 4, pp. 897-904 (2004).

Mochly-Rosen, "Localization of protein kinases by anchoring proteins: a theme in signal transduction", Science, vol. 268, No. 5208, pp. 247-251 (1995).

Mochly-Rosen et al., "Pharmacological regulation of network kinetics by protein kinase C localization", Semin. Immunol., vol. 12, No. 1, pp. 55-61 (2000).

Mochly-Rosen et al., "Modulating protein kinase C signal transduction", Adv. Pharmacol., vol. 44, pp. 91-145 (1998).

(56) References Cited

OTHER PUBLICATIONS

Mochly-Rosen et al., "Spontaneous occurrence of an inhibitor of protein kinase C localization in a thyroid cancer cell line: role in thyroid tumorigenesis", Adv. Enzyme. Regul., vol. 41, pp. 87-97 (2001).
Mochly-Rosen et al., "A protein kinase C isozyme is translocated to cytoskeletal elements on activation", Cell Regul., vol. 1, No. 9, pp. 693-706 (1990).
Mochly-Rosen et al., "Cardiotrophic effects of protein kinase C epsilon: analysis by in vivo modulation of PKCepsilon translocation", Circ. Res., vol. 86, No. 11, pp. 1173-1179 (2000).
Mochly-Rosen et al., "Intraction of protein kinase C with RACK1, a receptor for activated C-kinase: A role in beta protein kinase C mediated signal transduction", Biochem. Soc. Trans., vol. 23, No. 3, p. 596-600 (1995).
Mochly-Rosen et al., "Anchoring proteins for protein kinase C: A means for isozyme selectivity", Faseb J., vol. 12, No. 1, p. 35-42 (1998).
Mochly-Rosen et al., "p65 fragments homologous to the C2 region of protein kinase C, bind to the intracellular receptors for protein kinase C", Biochemistry, vol. 31, No. 35, p. 8120-8124 (1992).
Mochly-Rosen et al., "Intracellular receptors for activated protein kinase C: Identification of a binding site for the enzyme", J. Biol. Chem., vol. 266, No. 23, p. 14866-14868 (1991).
Mochly-Rosen et al., "Identification of intracellular receptor proteins for activated protein kinase C", PNAS, vol. 88, p. 3997-4000 (1991).
Moon et al., "KR-31378, a novel benzopyran analog, attenuates hypoxia-induced cell death via mitochondrial KATP channel and protein kinase C-epsilon in heart-derived H9c2 cells", Eur. J. Pharmacol., vol. 506, No. 1, pp. 27-35 (2004).
Murriel et al., "Opposing roles of delta and epsilonPKC in cardiac ischemia and reperfusion: targeting the apoptotic machinery", Arch. Biochem. Biophys., vol. 420, No. 2, pp. 246-254 (2003).
Murriel et al., "Protein kinase Cdelta activation induces apoptosis in response to cardiac ischemia and reperfusion damage: A mechanism involving BAD and the mitochondria", J. Biol. Chem., vol. 279, No. 46, p. 47985-47991 (2004).
Nelson et al., "Ethanol-induced phosphorylation and potentiation of the activity of type 7 adenylyl cyclase. Involvement of protein kinase C delta", J. Biol. Chem., vol. 278, No. 7, pp. 4552-4560 (2003).
Newton and Messing, "Intracellular signaling pathways that regulate behavioral responses to ethanol", Pharmacol. Ther., vol. 109, No. 1-2, pp. 227-237 (2006).
Newton and Ron, "Protein kinase C and alcohol addiction", Pharmacol. Res., vol. 55, No. 6, pp. 570-577 (2007).
Nguyen et al., "Investigation of PKC isoform-specific translocation and targeting of the current of the late afterhyperpolarizing potential of myenteric AH neurons", Euro. J. Nuerosci., vol. 21, No. 4, pp. 905-913 (2005).
Novalija et al., "Reactive oxygen species precede the epsilon isoform of protein kinase C in the anesthetic preconditioning signaling cascade", Anasthesiology, vol. 99, No. 2, pp. 421-428 (2003).
Ogbi and Johnson, "Protein kinase Cepsilon interacts with cytochrome c oxidase subunit IV and enhances cytochrome c oxidase activity in neonatal cardiac myocyte preconditioning", Biochem. J. vol. 393(Pt. 1), pp. 191-199 (2006).
Okochi et al., "Diverse regulation of sensory signaling by C. elegans nPKC-epsilon/eta TTX-4", EMBO J. vol. 24, No. 12, pp. 2127-2137 (2005).
Parada et al., "Transient attenuation of protein kinase Cepsilon can terminate a chronic hyperalgesic state in the rat", Neuroscience, vol. 120, No. 1, pp. 219-226 (2003).
Parada et al., "Chronic hyperalgesic priming in the rat involves a novel interaction between cAMP and PKCepsilon second messenger pathways", Pain, vol. 113, No. 1-2, pp. 185-190 (2005).
Pardo et al. "FGF-2 protects small cell lung cancer cells from apoptosis through a complex involving PKCepsilon, B-Raf and S6K2", EMBO J. vol. 25, No. 13, pp. 3078-3088 (2006).
Park et al., "Angiotensin II inhibits inward rectifier K+ channels in rabbit coronary arterial smooth muscle cells through protein kinase Calpha", Biochem. Biophys. Res. Commun., vol. 341, No. 3, pp. 728-735 (2006).
Pastori et al., "Delivery of proteins and peptides into live cells by means of protein transduction domains: potential application to organ and cell transplantation", Transplantation, vol. 77, No. 11, p. 1627-1631 (2004).
Perez-Pinzon et al., "Role of reactive oxygen species and protein kinase C in ischemic tolerance in the brain", Antioxid. Redox. Signal, vol. 7, No. 9-10, pp. 1150-1157 (2005).
Perry et al., "PMA- and ANG II-induced PKC regulation of the renal Na+-HCO3-cotransporter (hkNBCe1)", Am. J. Physiol Renal Physiol., vol. 290, No. 2, pp. F417-F427 (2006).
Pierre et al., "Ouabain triggers preconditioning through activation of the Na+,K+-ATPase signaling cascade in rat hearts", Cardiovasc. Res., vol. 73, pp. 488-496 (2007).
Pitchford et al., "Nicotinic acetylcholine receptor desensitization is regulated by activation-induced extracellular adenosine accumulation", J. Neurosci., vol. 12, No. 11, p. 4540-4544 (1992).
Poole et al., "Inflammation and inflammatory agents activate protein kinase C epsilon translocation and excite guinea-pig submucosal neurons", Gastroenterology, vol. 133, No. 4, pp. 1229-1239 (2007).
Poole and Furness, "PKC delta-isoform translocation and enhancement of tonic contractions of gastrointestinal smooth muscle", Am. J. Physiol., vol. 292, No. 3, pp. G887-G898 (2006).
Qi et al., "Protein kinase C epsilon regulates gamma-aminobutyrate type A receptor sensitivity to ethanol and benzodiazepines through phosphorylation of gamma2 subunits", J. Biol. Chem., vol. 282, No. 45, pp. 33052-33063 (2007).
Raval et al., "EpsilonPKC phosphorylates the mitochondrial K(+) (ATP) channel during induction of ischemic preconditioning in the rat hippocampus", Brain Res., vol. 1184, pp. 345-353 (2007).
Raval et al., "Protein kinase C delta cleavage initiates an aberrant signal transduction pathway after cardiac arrest and oxygen glucose deprivation", J. Cereb. Blood Flow Metab., vol. 25, No. 6, pp. 730-741 (2005).
Raval et al., "Epsilon PKC is required for the induction of tolerance by ischemic and NMDA-mediated preconditioning in the organotypic hippocampal slice", J. Neirosci., vol. 23, No. 2, p. 384-391 (2003).
Ridge et al., "Dopamine-induced exocytosis of Na.K-ATPase is dependent on activation of protein kinase C-epsilon and -delta", Mol. Biol. Cell., vol. 13, No. 4, p. 1381-1389 (2002).
Ridge et al., "Keratin 8 phosphorylation by protein kinase C delta regulates shear stress-mediated disassembly of keratin intermediate filaments in alveolar epithelial cells", J. Biol. Chem., vol. 280, No. 34, pp. 30400-30405 (2005).
Robia et al., "Novel determinant of PKC-epsilon anchoring at cardiac Z-lines", Am. J. Physiol. Heart Circ. Physiol., vol. 289, No. 5, pp. H1941-H1950 (2005).
Rodriguez et al., "Characterization of the binding and phosphorylation of cardiac calsequestrin by epsilon protein kinase C", FEBS Lett., vol. 454, No. 3, pp. 240-246 (1999).
Rodriguez et al., "RACK 1, a protein kinase C anchoring protein, coordinates the binding of activated protein kinase C and select pleckstrin homology domains in vitro", Biochemistry, vol. 38, No. 42, pp. 13787-13794 (1999).
Ron et al., "Cloning of an intracellular receptor for protein kinase C: a homolog of the beta subunit of G proteins", Proc. Natl. Acad. Sci. USA, vol. 91, No. 3, pp. 839-843 (1994).
Ron et al., "C2 region-derived peptides inhibit translocation and function of beta protein kinase C in vivo", J. Biol. Chem., vol. 270, No. 41, pp. 24180-24187 (1995).
Ron et al., "An autoregulatory region in protein kinase C: the pseudo anchoring site", Proc. Natl. Acad. Sci. USA, vol. 92, No. 2, pp. 492-496 (1995).
Ron and Mochly-Rosen, "Agonists and antagonists of protein kinase C function, derived from its binding proteins", J. Biol. Chem., vol. 269, No. 34, p. 21395-21398 (1994).

(56) References Cited

OTHER PUBLICATIONS

Satoh et al., "PKC-delta and -epsilon regulate NF-kappaB activation induced by cholecystokinin and TNF-alpha in pancreatic acinar cells", Am. J. Physiol. Gastrointest. Liver Physiol., vol. 287, No. 3, p. G582-G591 (2004).

Satoh et al., "Tumor necrosis factor-alpha mediates pancreatitis responses in acinar cells via protein kinase C and proline-rich tyrosine kinase 2", Gastroenterology, vol. 129, No. 2, pp. 639-651 (2005).

Schechtman and Mochly-Rosen, "Isozyme-specific inhibitors and activators of protein kinase C", Methods Enzymol., vol. 345, pp. 470-489 (2002).

Schechtman et al., "A critical intramolecular interaction for protein kinase Cepsilon translocation", J. Biol. Chem., vol. 279, No. 16, pp. 15831-15840 (2004).

Schechtman et al., "Adaptor proteins in protein kinase C-mediated signal transduction", Oncogene, vol. 20, No. 44, pp. 6339-6347 (2001).

Schechtman et al., "Overlay method for detecting protein-protein interactions", Methods Mol. Biol., vol. 233, pp. 351-357 (2003).

Schechtman et al., "Glutathione S-transferase pull-down assay", Methods Mol. Biol., vol. 233, pp. 345-350 (2003).

Schmitz-Peiffer et al., "Inhibition of PKCepsilon improves glucose-stimulated insulin secretion and reduces insulin clearance", Cell Metab., vol. 6, No. 4, pp. 320-328 (2007).

Shao et al., "Hypothermia-induced cardioprotection using extended ischemia and early reperfusion cooling", Am. J. Physiol. Circ. Physiol., vol. 292, No. 4, pp. H1995-H2003 (2007).

Shimoni and Liu, "Role of PKC in autocrine regulation of rat ventricular K+ currents by angiotensin and endothelin", Am. J. Physiol. Heart Circ. Physiol., vol. 284, No. 4, pp. H1168-H1181 (2003).

Shizukuda and Buttrick, et al., "Protein kinase C(epsilon) modulates apoptosis induced by beta-adrenergic stimulation in adult rat ventricular myocytes via extracellular signal-regulated kinase (ERK) activity", J. Mol. Cell Cardiol., vol. 33, No. 10, pp. 1791-1803 (2001).

Shizukuda et al., "Protein kinase C-delta modulates apoptosis induced by hyperglycemia in adult ventricular myocytes", Am. J. Physiol. Heart Circ. Physiol., vol. 282, No. 5, pp. H1625-H1634 (2002).

Shumilla et al., "Ethanol withdrawal-associated allodynia and hyperalgesia: age-dependent regulation by protein kinase C epsilon and gamma isoenzymes", J. Pain, vol. 6, No. 8, pp. 535-549 (2005).

Shumilla et al. "Inhibition of spinal protein kinase C-epsilon or -gamma isozymes does not affect halothane minimum alveolar anesthetic concentration in rats", Anesth. Analg., vol. 99, No. 1, pp. 82-84 (2004).

Silva et al., "*Salmonella typhimurium* SipA-induced neutrophil transepithelial migration: involvement of a PKC-alpha-dependent signal transduction pathway", Am. J. Physiol. Gastrointest. Liver Physiol., vol. 286, No. 6, pp. G1024-G1031 (2004).

Simon et al., "The identification and purification of a manunalian-like protein kinase C in the yeast *Saccharomyces cerevisiae*", Proc. Biol. Sci., vol. 243, No. 1307, pp. 165-171 (1991).

Simon et al., "Characterization of PKC2, a gene encoding a second protein kinase C isotype of *Saccharomyces cerevisiae*", Curr. Biol., vol. 3, No. 12, pp. 813-821 (1993).

Smith et al., "The HIY nefprotein associates with protein kinase C theta", J. Biol. Chem., vol. 271, No. 28, pp. 16753-16757 (1996).

Smith et al., "Inhibition of protein kinase C function by injection of intracellular receptors for the enzyme", Biochem. Biophys. Res. Commun., vol. 188, No. 3, pp. 1235-1240 (1992).

Smith et al., "Determination of the role of conventional, novel and atypical PKC isoforms in the expression of morphine tolerance in mice", Pain, vol. 127, No. 1-2, pp. 129-139 (2007).

Souroujon et al., "Peptide modulators of protein-protein interactions in intracellular signaling", Nat. Biotechnol., vol. 16, No. 10, pp. 919-924 (1998).

Souroujon et al., "State-specific monoclonal antibodies identifY an intermediate state in epsilon protein kinase C activation", J. Biol. Chem., vol. 279, No. 17, pp. 17617-17624 (2004).

Stebbins et al., "Binding specificity for RACK 1 resides in the V5 region of beta II protein kinase c", J. Biol. Chem., vol. 276,. No. 32, pp. 29644-29650 (2001).

Steinberg et al., "A protein kinase Cepsilon-anti-apoptotic kinase signaling complex protects human vascular endothelial cells against apoptosis through induction of Bcl-2", J. Biol. Chem., vol. 282, No. 44, pp. 32288-32297 (2007).

Summer et al., "Enhanced inflammatory hyperalgesia after recovery from burn injury", Burns, vol. 33, No. 8, pp. 1021-1026 (2007).

Summer et al.,. "TrkA and PKC-epsilon in thermal burn-induced mechanical hyperalgesia in the rat", J. Pain, vol. 7, No. 12, pp. 884-891 (2006).

Suzuki et al., "Role of phospholipase Cgamma-induced activation of protein kinase Cepsilon (PKCepsilon) and PKCbetal in epidermal growth factor-mediated protection of tight junctions from acetaldehyde in Caco-2 cell monolayers", J. Biol. Chem., vol. 283, No. 6, pp. 3574-3583 (2008).

Sweitzer et al., "Protein kinase C epsilon and ganuna: involvement in formalin-induced nociception in neonatal rats", J. Pharmacol. Exp. Ther. 309(2): 616-625 (2004).

Sweitzer et al., "Exaggerated nociceptive responses on morphine withdrawal: roles of protein kinase C epsilon and ganuna", Pain, vol. 110, No. 1-2, pp. 281-289 (2004).

Szabo et al., "RSA 2004: combined basic research satellite symposium—session three: alcohol and mitochondrial metabolism: at the crossroads of life and death", Alcohol Clin. Exp. Res., vol. 29, No. 9, pp. 1749-1752 (2005).

Tabakoff et al., "Phosphorylation cascades control the actions of ethanol on cell cAMP signalling", J. Biomed. Sci., vol. 8, No. 1, pp. 44-51 (2001).

Tanaka et al., "Suppression of graft coronary artery disease by a brief treatment with a selective epsilonPKC activator and a deltaPKC inhibitor in murine cardiac allografts", Circulation, vol. 110, No. 11, Suppl. 1, p. II194-II199 (2004).

Tanaka et al., "Inhibition of heart transplant injury and graft coronary artery disease after prolonged organ ischemia by selective protein kinase C regulators", J. Thorac. Cardiovasc. Surg., vol. 129, No. 5, pp. 1160-1167 (2005).

Taneja et al., "Proinflammatory interleukin-1 cytokines increase mesangial cell hexokinase activity and hexokinase II isoform abundance", Am. J. Physiol. Cell Physiol., vol. 287, No. 2, pp. C548-C557 (2004).

Tepperman et al., "Effect of protein kinase C activation on intracellular Ca2+ signaling and integrity of intestinal epithelial cells", Eur. J. Pharmacol., vol. 518, No. 1, pp. 1-9 (2005).

Toda et al., "Stimulatory action of protein kinase C(epsilon) isoform on the slow component of delayed rectifier K+ current in guinea-pig atrial", British J. Pharmacol., vol. 150, No. 8, pp. 1011-1021 (2007).

Vallentin and Mochly-Rosen, "RBCK1, a protein kinase Cbetal (PKCbetal)-interacting protein, regulates PKCbeta-dependent function", J. Biol. Chem., vol. 282, No. 3, pp. 1650-1657 (2007).

Van Baal, et al., "Translocation of diacylglycerol kinase theta from cytosol to plasma membrane in response to activation of G protein-coupled receptors and protein kinase C", vol. 280, No. 11, pp. 9870-9878 (2005).

Van Kolen et al., "Nociceptive and behavioural sensitisation by protein kinase Cepsilon signalling in the CNS", J. Neurochem., vol. 104, No. 1, pp. 1-13 (2007).

Velazquez et al., "Protein kinase C in pain: involvement of multiple isoforms", Pharmacol. Res., vol. 55, No. 6, pp. 578-589 (2007).

Wang et al., "Protein kinase C-epsilon is a trigger of delayed cardioprotection against myocardial ischemia of kappa-opioid receptor stimulation in rat ventricular myocytes", J. Pharmacol. Exp. Ther., vol. 299, No. 2, pp. 603-610 (2001).

Wang et al., "Cell-specific role for epsilon- and betal-protein kinase C isozymes in protecting cortical neurons and astrocytes from ischemia-like injury", Neuropharmacology, vol. 47, No. 1, pp. 136-145 (2004).

(56) References Cited

OTHER PUBLICATIONS

Wang et al., "Endogenous calcitonin gene-related peptide protects human alveolar epithelial cells through protein kinase Cepsilon and heat shock protein", J. Biol. Chem., vol. 280, No. 21, pp. 20325-20330 (2005).

Way et al., "Identification of PKC-isophorm-specific biological actions using pharmacological approaches", TIPS, vol. 21, No. 5, pp. 181-187 (2000).

Webb et al., "Protein kinase C-epsilon promotes adipogenic commitment and is essential for terminal differentiation of 3T3-F442A preadipocytes", Cell Mol. Life Sci., vol. 60, No. 7, pp. 1504-1512 (2003).

Wu et al., "Epsilon protein kinase C in pathological myocardial hypertrophy. Analysis by combined transgenic expression of translocation modifiers and Galphaq", J. Biol. Chem., vol. 275, No. 39, pp. 29927-29930 (2000).

Xiao et al., "Evidence for functional role of epsilonPKC isozyme in the regulation of cardiac Na(+) channels", Am. J. Physiol. Cell. Physiol., vol. 281, No. 5, pp. C1477-C1486 (2001).

Xiao et al., "PKC isozyme selective regulation of cloned human cardiac delayed slow rectifier K current", Biochem. Biophys. Res. Commun., vol. 306, No. 4, pp. 1019-1025 (2003).

Yamamoto et al., "Endothelin-1 enhances capsaicin-evoked intracellular Ca2+ response via activation of endothelin a receptor in a protein kinase Cepsilon-dependent manner in dorsal root ganglion neurons", Nuerosci., vol. 137, pp. 949-960 (2006).

Yamamura et al., "Protein kinase C and preconditioning: role of the sarcoplasmic reticulum", Am. J. Physiol. Heart Circ. Physiol., vol. 289, No. 6, pp. H2484-H2490 (2005).

Yedovitzky et al., "Translocation inhibitors define specificity of protein kinase C isoenzymes in pancreatic beta-cells", J. Biol. Chem., vol. 272, No. 3, pp. 1417-1420 (1997).

Zatta et al., "Infarct-sparing effect of myocardial postconditioning is dependent on protein kinase C signalling", Cardiovasc. Res., vol. 70, No. 2, pp. 315-324 (2006).

Zhang et al., "C2 region-derived peptides of beta-protein kinase C regulates cardiac Ca2+ channels", Circ. Res., vol. 80, No. 5, p. 720-729 (1997).

Zhang et al., "Role of nitric-oxide synthase, free radicals, and protein kinase C delta in opioid-induced cardioprotection", J. Pharmacol. Exp. Ther., vol. 301, No. 3, pp. 1012-1019 (2002).

Zhang et al., "PKC isoform-specific enhancement of capacitative calcium entry in human corneal epithelial cells", Invest. Opthamol. Vis. Sci., vol. 47, No. 9, pp. 3989-4000 (2006).

Zhang et al., "Neurokinin-1 receptor enhances TRPV1 activity in primary sensory neurons via PKCepsilon: a novel pathway for heat hyperalgesia", J. Neurosci., vol. 27, No. 44, pp. 12067-12077 (2007).

Zhong et al., "Regulation of volume-sensitive outwardly rectifying anion channels in pulmonary arterial smooth muscle cells by PKC", Am. J. Physiol. Cell Physiol., vol. 283, No. 6, pp. C1627-C1636 (2002).

Zhou et al., "Differential activation of protein kinase C isozymes by phorbol ester and collagen in human skin microvascular endothelial cells", J. Invest. Dermatol., vol. 107, No. 2, pp. 248-252 (1996).

Zhou et al., "Moderate alcohol consumption induces sustained cardiac protection by activating PKC-epsilon and Akt", Am. J. Physiol. Heart Circ. Physiol., vol. 282, No. 1, pp. H165-H174 (2002).

\* cited by examiner

Figure 4

B
Ac-GKLFIMNLGYGRKKRRQRRR-NH2

A
CKLFIMN
|
CYGRKKRRQRRR

Figure 16

KP-1680   H-  EAVSLKPTGGYGRKKRRQRRR- OH

KP-1681   Ac- EAVSLKPTGGYGRKKRRQRRR- OH

KP-1633   H-  EAVSLKPTGGYGRKKRRQRRR- NH2

KP-1678   Ac- EAVSLKPTGGYGRKKRRQRRR- NH2

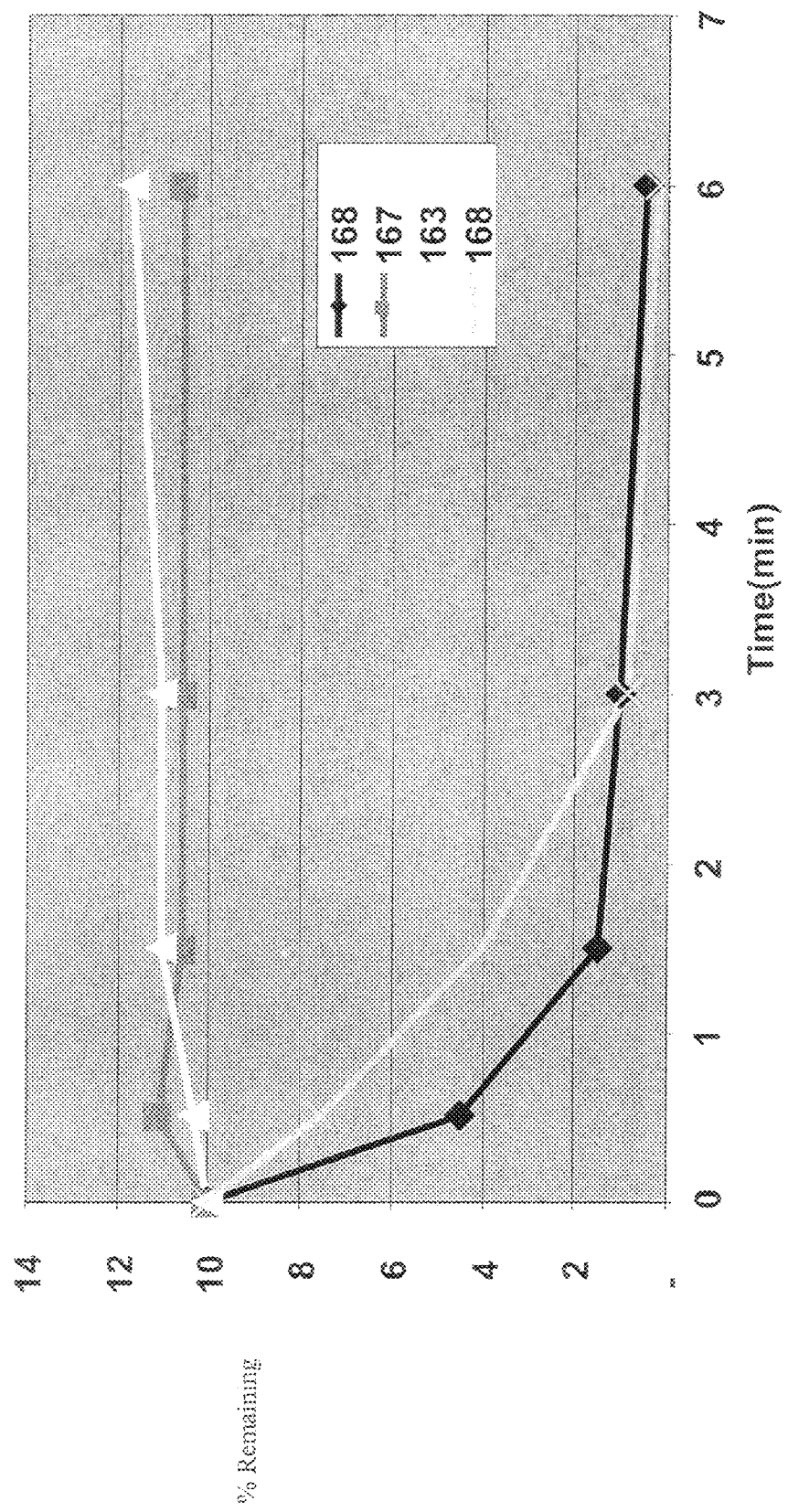

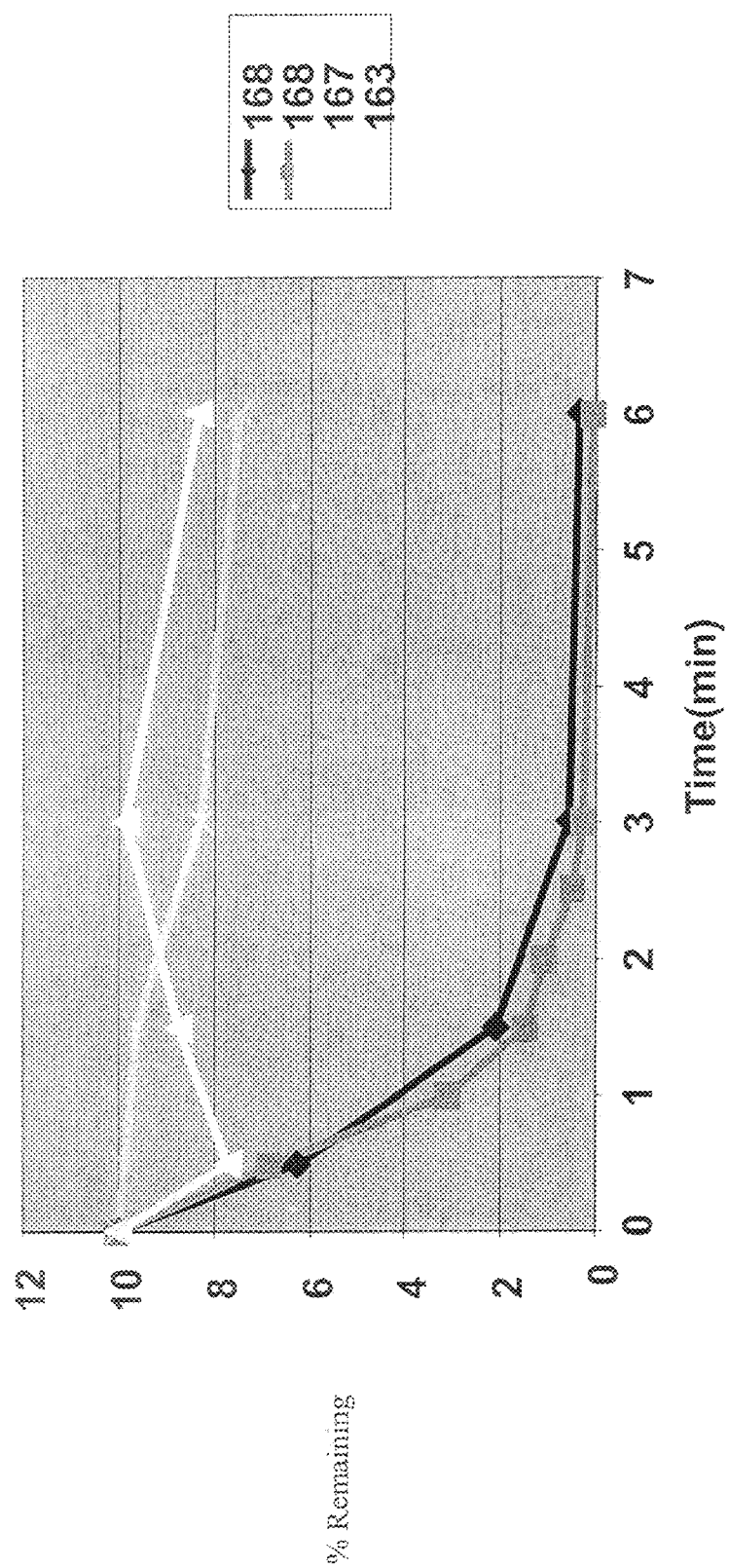

SEQUENCE LISTING

<160> NUMBER OF SEQ ID NOS: 172

<210> SEQ ID NO 1
<211> LENGTH: 11
<212> TYPE: PRT
<213> ORGANISM: Artificial Sequence
<220> FEATURE:

```
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 1

Cys Glu Leu Gly Ser Leu Gln Ala Glu Asp Asp
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 2

Ile Pro Glu Gly Asp Glu Glu Gly
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 3

Gln Leu Val Ile Ala Asn
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 4

Gly Leu Gly Ala Glu Asn
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 5

Ala Arg Gly Ala Glu Asn
1               5
```

```
<210> SEQ ID NO 6
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 6

Cys Gly Lys Gly Ala Glu Asn
 1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 7

Cys Gly Lys Gly Ala Glu Asn
 1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 8

Lys Gln Lys Thr Lys Thr Ile Lys
 1               5

<210> SEQ ID NO 9
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(13)
<223> OTHER INFORMATION: Cargo peptide

<400> SEQUENCE: 9

Met Asp Pro Asn Gly Leu Ser Asp Pro Tyr Val Lys Leu
 1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide
```

```
<400> SEQUENCE: 10

Ile Pro Asp Pro Lys Ser Glu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 11

Ser Leu Asn Pro Glu Trp Asn Glu Thr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 12

Val Pro Pro Glu Gly Ser Glu Ala
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 13

Lys Leu Phe Ile Met Asn
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 14

Arg Asp Lys Arg Asp Thr Ser
1               5

<210> SEQ ID NO 15
<211> LENGTH: 9
<212> TYPE: PRT
<213> ORGANISM: Artificial Sequence
```

```
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 15

Cys Ala Arg Asp Lys Arg Asp Thr Ser
 1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 16

Gly Arg Asp Lys Arg Asp Thr Ser
 1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 17

Ala Arg Asp Lys Arg Asp Thr Ser
 1               5

<210> SEQ ID NO 18
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(12)
<223> OTHER INFORMATION: Cargo peptide

<400> SEQUENCE: 18

Ala Arg Asp Lys Arg Asp Thr Ser Asn Phe Asp Lys
 1               5                  10

<210> SEQ ID NO 19
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(14)
<223> OTHER INFORMATION: Cargo peptide

<400> SEQUENCE: 19

Ala Gly Phe Ser Tyr Thr Asn Pro Glu Phe Val Ile Asn Val
 1               5                  10
```

```
<210> SEQ ID NO 20
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 20

Gln Glu Val Ile Arg Asn
 1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 21

Cys Gly Arg Asn Ala Glu
 1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 22

Ala Cys Gly Arg Asn Ala Glu
 1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 23

Ala Cys Gly Lys Asn Ala Glu
 1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
```

```
<223> OTHER INFORMATION: Cargo peptide

<400> SEQUENCE: 24

Lys Ala Cys Gly Arg Asn Ala Glu
 1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 25

Cys Gly Arg Asn Ala Glu Asn
 1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 26

Ala Cys Gly Arg Asn Ala Glu
 1               5

<210> SEQ ID NO 27
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(14)
<223> OTHER INFORMATION: Cargo peptide

<400> SEQUENCE: 27

Ser Phe Val Asn Ser Glu Phe Leu Lys Pro Glu Val Leu Ser
 1               5                  10

<210> SEQ ID NO 28
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 28

Val Ala Asp Ala Asp Asn Cys Ser
 1               5

<210> SEQ ID NO 29
<211> LENGTH: 6
<212> TYPE: PRT
```

```
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 29

Gly Arg Ser Gly Glu Asn
 1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 30

Gly Leu Ser Gly Glu Asn
 1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 31

Arg Leu Val Leu Ala Ser
 1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 32

Pro Cys Gly Arg Ser Gly Glu Asn
 1               5

<210> SEQ ID NO 33
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 33

Cys Ser Phe Asn Ser Tyr Glu Leu Gly Ser Leu
```

```
<210> SEQ ID NO 34
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 34

Ser Phe Asn Ser Tyr Glu Leu Gly Ser Leu
 1               5                  10

<210> SEQ ID NO 35
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 35

Thr Phe Asn Ser Tyr Glu Leu Gly Ser Leu
 1               5                  10

<210> SEQ ID NO 36
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 36

Ala Phe Asn Ser Asn Tyr Glu Leu Gly Ser Leu
 1               5                  10

<210> SEQ ID NO 37
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 37

Ser Phe Asn Ser Tyr Glu Leu Gly Thr Leu
 1               5                  10

<210> SEQ ID NO 38
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
```

```
<222> LOCATION: (1)...(10)
<223> OTHER INFORMATION: Cargo peptide

<400> SEQUENCE: 38

Ser Thr Asn Ser Tyr Glu Leu Gly Ser Leu
 1               5                  10

<210> SEQ ID NO 39
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 39

Ser Phe Asn Ser Phe Glu Leu Gly Ser Leu
 1               5                  10

<210> SEQ ID NO 40
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 40

Ser Asn Ser Tyr Asp Leu Gly Ser Leu
 1               5

<210> SEQ ID NO 41
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 41

Ser Phe Asn Ser Tyr Glu Leu Pro Ser Leu
 1               5                  10

<210> SEQ ID NO 42
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 42

Thr Phe Asn Ser Tyr Glu Leu Gly Thr Leu
 1               5                  10

<210> SEQ ID NO 43
<211> LENGTH: 10
```

```
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 43

Ser Phe Asn Ser Tyr Glu Ile Gly Ser Val
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 44

Ser Phe Asn Ser Tyr Glu Val Gly Ser Ile
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 45

Ser Phe Asn Ser Tyr Glu Leu Gly Ser Val
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 46

Ser Phe Asn Ser Tyr Glu Leu Gly Ser Ile
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 47
```

```
Ser Phe Asn Ser Tyr Glu Ile Gly Ser Leu
  1               5                  10

<210> SEQ ID NO 48
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 48

Ser Phe Asn Ser Tyr Glu Val Gly Ser Leu
  1               5                  10

<210> SEQ ID NO 49
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 49

Ala Phe Asn Ser Tyr Glu Leu Gly Ser Leu
  1               5                  10

<210> SEQ ID NO 50
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 50

Tyr Asp Leu Gly Ser Leu
  1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 51

Phe Asp Leu Gly Ser Leu
  1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic construct
<220> FEATURE:
```

```
<221> NAME/KEY: DOMAIN
<222> LOCATION: (1)...(6)
<223> OTHER INFORMATION: Cargo peptide

<400> SEQUENCE: 52

Tyr Asp Ile Gly Ser Leu
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 53

Tyr Asp Val Gly Ser Leu
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 54

Tyr Asp Leu Pro Ser Leu
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 55

Tyr Asp Leu Gly Leu Leu
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 56

Tyr Asp Leu Gly Ser Ile
1               5

<210> SEQ ID NO 57
```

```
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 57

Tyr Asp Leu Gly Ser Val
 1               5

<210> SEQ ID NO 58
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(4)
<223> OTHER INFORMATION: Cargo peptide

<400> SEQUENCE: 58

Ile Gly Ser Leu
 1

<210> SEQ ID NO 59
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(4)
<223> OTHER INFORMATION: Cargo peptide

<400> SEQUENCE: 59

Val Gly Ser Leu
 1

<210> SEQ ID NO 60
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(4)
<223> OTHER INFORMATION: Cargo peptide

<400> SEQUENCE: 60

Leu Pro Ser Leu
 1

<210> SEQ ID NO 61
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(4)
<223> OTHER INFORMATION: Cargo peptide

<400> SEQUENCE: 61
```

```
Leu Gly Leu Leu
 1

<210> SEQ ID NO 62
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(4)
<223> OTHER INFORMATION: Cargo peptide

<400> SEQUENCE: 62

Leu Gly Ser Ile
 1

<210> SEQ ID NO 63
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(4)
<223> OTHER INFORMATION: Cargo peptide

<400> SEQUENCE: 63

Leu Gly Ser Val
 1

<210> SEQ ID NO 64
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 64

Ala Leu Ser Thr Glu Arg Gly Lys Thr Leu Val
 1               5                  10

<210> SEQ ID NO 65
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 65

Ala Leu Ser Thr Asp Arg Gly Lys Thr Leu Val
 1               5                  10

<210> SEQ ID NO 66
<211> LENGTH: 11
<212> TYPE: PRT
<213> ORGANISM: Artificial Sequence
<220> FEATURE:
<223> OTHER INFORMATION: Synthetic construct
```

```
<220> FEATURE:
<221> NAME/KEY: DOMAIN
<222> LOCATION: (1)...(11)
<223> OTHER INFORMATION: Cargo peptide

<400> SEQUENCE: 66

Ala Leu Thr Ser Asp Arg Gly Lys Thr Leu Val
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic construct

<400> SEQUENCE: 67

Ala Leu Thr Thr Asp Arg Gly Lys Ser Leu Val
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 68

Ala Leu Thr Thr Asp Arg Pro Lys Thr Leu Val
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 69

Ala Leu Thr Thr Asp Arg Gly Arg Thr Leu Val
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 70

Ala Leu Thr Thr Asp Lys Gly Lys Thr Leu Val
1               5                   10

<210> SEQ ID NO 71
<211> LENGTH: 11
<212> TYPE: PRT
<213> ORGANISM: Artificial Sequence
```

```
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 71

Ala Leu Thr Thr Asp Lys Gly Lys Thr Leu Val
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 72

Val Leu Met Arg Ala Ala Glu Glu Pro Val
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 73

Gln Ser Met Arg Ser Glu Asp Glu Ala Lys
1               5                   10

<210> SEQ ID NO 74
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 74

Gln Gly Phe Glu Lys Lys Thr Gly Val
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 75

Asp Asn Asn Gly Thr Tyr Gly Lys Ile
1               5
```

```
<210> SEQ ID NO 76
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 76

Lys Asn Leu Ile Asp Ser
 1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 77

Val Lys Ser Pro Arg Asp Tyr Ser
 1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 78

Val Lys Ser Pro Cys Arg Asp Tyr Ser
 1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 79

Ile Lys Ser Pro Arg Leu Tyr Ser
 1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
```

<223> OTHER INFORMATION: Cargo peptide

<400> SEQUENCE: 80

Lys Asn Leu Ile Asp Ser
 1               5

<210> SEQ ID NO 81
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 81

Pro Lys Val Lys Ser Pro Arg Asp Tyr Ser Asn
 1               5                  10

<210> SEQ ID NO 82
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 82

Asn Gly Leu Leu Lys Ile Lys
 1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 83

Glu Ala Val Ser Leu Lys Pro Thr
 1               5

<210> SEQ ID NO 84
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 84

Leu Ala Val Phe His Asp Ala Pro Ile Gly Tyr
 1               5                  10

<210> SEQ ID NO 85
<211> LENGTH: 9
<212> TYPE: PRT

```
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 85

Asp Asp Phe Val Ala Asn Cys Thr Ile
1               5

<210> SEQ ID NO 86
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 86

Trp Ile Asp Leu Glu Pro Glu Gly Arg Val
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 87

His Ala Val Gly Pro Arg Pro Gln Thr Phe
1               5                   10

<210> SEQ ID NO 88
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 88

Asn Gly Ser Arg His Phe Glu Asp
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 89

His Asp Ala Pro Ile Gly Tyr Asp
```

-continued

```
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 90

His Asp Ala Pro Ile Gly
1               5

<210> SEQ ID NO 91
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 91

His Asp Ala Ala Ile Gly Tyr Asp
1               5

<210> SEQ ID NO 92
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 92

His Asp Ala Pro Ile Pro Tyr Asp
1               5

<210> SEQ ID NO 93
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 93

His Asn Ala Pro Ile Gly Tyr Asp
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
```

```
<222> LOCATION: (1)...(8)
<223> OTHER INFORMATION: Cargo peptide

<400> SEQUENCE: 94

His Ala Ala Pro Ile Gly Tyr Asp
 1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 95

Ala Asp Ala Pro Ile Gly Tyr Asp
 1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 96

His Asp Ala Pro Ala Gly Tyr Asp
 1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 97

His Asp Ala Pro Ile Gly Ala Asp
 1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 98

His Asp Ala Pro Ile Ala Tyr Asp
 1               5

<210> SEQ ID NO 99
<211> LENGTH: 8
```

```
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 99

His Asp Ala Pro Ile Gly Tyr Ala
 1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 100

Ser Ser Pro Ser Glu Glu Asp Arg Ser
 1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 101

Pro Cys Asp Gln Glu Ile Lys Glu
 1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 102

Glu Asn Asn Ile Arg Lys Ala Leu Ser
 1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 103
```

Gly Glu Val Arg Gln Gly Gln Ala
1               5

<210> SEQ ID NO 104
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 104

Glu Ala Ile Val Lys Gln
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 105

Ile Lys Thr Lys Arg Asp Val
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 106

Ile Lys Thr Lys Arg Leu Ile
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 107

Cys Glu Ala Ile Val Lys Gln
1               5

<210> SEQ ID NO 108
<211> LENGTH: 10
<212> TYPE: PRT
<213> ORGANISM: Artificial Sequence
<220> FEATURE:
<223> OTHER INFORMATION: Synthetic construct
<220> FEATURE:

```
<221> NAME/KEY: DOMAIN
<222> LOCATION: (1)...(10)
<223> OTHER INFORMATION: Cargo peptide

<400> SEQUENCE: 108

Thr Lys Arg Asp Val Asn Asn Phe Asp Gln
 1               5                  10

<210> SEQ ID NO 109
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 109

Val Arg Leu Lys Ala His Tyr
 1               5

<210> SEQ ID NO 110
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 110

Val Asp Ser Glu Gly Asp
 1               5

<210> SEQ ID NO 111
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 111

Val Phe Pro Ser Ile Pro Glu Gln
 1               5

<210> SEQ ID NO 112
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(15)
<223> OTHER INFORMATION: Cargo peptide

<400> SEQUENCE: 112

Ser Gln Glu Pro Pro Val Asp Asp Lys Asn Glu Asp Ala Asp Leu
 1               5                  10                  15

<210> SEQ ID NO 113
```

```
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 113

Ile Lys Asp Asp Ser Glu Asp
 1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 114

Pro Val Ile Asp Gly Met Asp Gly Ile
 1               5

<210> SEQ ID NO 115
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 115

Glu Asp Ala Ile Lys Arg
 1               5

<210> SEQ ID NO 116
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(5)
<223> OTHER INFORMATION: Cargo peptide

<400> SEQUENCE: 116

Glu Asp Ala Ile Arg
 1               5

<210> SEQ ID NO 117
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 117
```

```
Ile Thr Asp Asp Tyr Gly Leu Asp
1               5

<210> SEQ ID NO 118
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 118

Ile Thr Asp Asp Tyr Gly Asp Leu
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 119

Asp Asp Tyr Gly Leu Asp Asn
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 120

Asn Gly Tyr Leu Arg Val Arg
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 121

Glu Ala Val Gly Leu Gln Pro Thr
1               5

<210> SEQ ID NO 122
<211> LENGTH: 11
<212> TYPE: PRT
<213> ORGANISM: Artificial Sequence
<220> FEATURE:
<223> OTHER INFORMATION: Synthetic construct
```

```
<220> FEATURE:
<221> NAME/KEY: DOMAIN
<222> LOCATION: (1)...(11)
<223> OTHER INFORMATION: Cargo peptide

<400> SEQUENCE: 122

Leu Ala Val Phe His Glu Thr Pro Leu Gly Tyr
1               5                   10

<210> SEQ ID NO 123
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 123

Asp Phe Val Ala Asn Cys Thr Leu
1               5

<210> SEQ ID NO 124
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 124

Trp Val Asp Leu Glu Pro Glu Gly Lys Val
1               5                   10

<210> SEQ ID NO 125
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 125

His Ser Leu Phe Lys Lys Gly His
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 126

Thr Gly Ala Ser Asp Thr Phe Glu Gly
1               5
```

```
<210> SEQ ID NO 127
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 127

Glu Gly His Leu Pro Met
1               5

<210> SEQ ID NO 128
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 128

Glu Gly His Asp Pro Met
1               5

<210> SEQ ID NO 129
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 129

Ile Lys Ser Arg Glu Asp Val Ser
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 130

Val Arg Ser Arg Glu Asp Val Ser
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide
```

```
<400> SEQUENCE: 131

Pro Arg Ile Lys Ser Arg Glu Asp Val
1               5

<210> SEQ ID NO 132
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 132

His Gln Val Arg Val Lys Ala Tyr Tyr Arg
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 133

Tyr Glu Leu Asn Lys Asp Ser Glu Leu Leu Ile
1               5                   10

<210> SEQ ID NO 134
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(15)
<223> OTHER INFORMATION: Cargo peptide

<400> SEQUENCE: 134

Met Asp Gln Ser Ser Met His Ser Asp His Ala Gln Thr Val Ile
1               5                   10                  15

<210> SEQ ID NO 135
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 135

Leu Asp Gln Val Gly Glu Glu
1               5

<210> SEQ ID NO 136
<211> LENGTH: 9
<212> TYPE: PRT
<213> ORGANISM: Artificial Sequence
<220> FEATURE:
```

```
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 136

Glu Ala Met Asn Thr Arg Glu Ser Gly
 1               5

<210> SEQ ID NO 137
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 137

Asp Asp Ile Val Arg Lys
 1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 138

Val Lys Leu Cys Asp Phe Gly Phe
 1               5

<210> SEQ ID NO 139
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 139

Ile Arg Leu Cys Asp Phe Ala Phe
 1               5

<210> SEQ ID NO 140
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 140

Gln Val Lys Leu Cys Asp Phe Gly Phe Ala
 1               5                  10
```

```
<210> SEQ ID NO 141
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 141

Met Ser Val Pro Pro Leu Leu Arg Pro
 1               5

<210> SEQ ID NO 142
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 142

Lys Phe Pro Glu Cys Gly Phe Tyr Gly Leu Tyr
 1               5                  10

<210> SEQ ID NO 143
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 143

Asp Pro Asp Ala Asp Gln Glu Asp Ser
 1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 144

Ser Lys Asp Thr Leu Arg Lys Arg His
 1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide
```

<400> SEQUENCE: 145

Ile Thr Leu Phe Gln Asn Asp Thr Gly
1               5

<210> SEQ ID NO 146
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 146

Gly Ser Asn Ser His Lys Asp Ile Ser
1               5

<210> SEQ ID NO 147
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 147

Ser Asp Ser Pro Glu Ala
1               5

<210> SEQ ID NO 148
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 148

Gly Leu Ser Asn Phe Asp Cys Gly
1               5

<210> SEQ ID NO 149
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Cargo peptide

<400> SEQUENCE: 149

Tyr Val Glu Ser Glu Asn Gly Gln Met Tyr Ile
1               5                   10

<210> SEQ ID NO 150
<211> LENGTH: 10
<212> TYPE: PRT
<213> ORGANISM: Artificial Sequence

```
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 150

Ile Val Lys Gly Lys Asn Val Asp Leu Ile
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 151

Asp Met Asn Glu Phe Glu Thr Glu Gly Phe
1               5                   10

<210> SEQ ID NO 152
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 152

Cys Ser Ile Lys Asn Glu Ala Arg Leu
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 153

Gly Lys Arg Glu Pro Gln Gly Ile Ser
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 154

Asp Glu Val Asp Lys Met Cys His Leu
1               5
```

<210> SEQ ID NO 155
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 155

Arg Ala Leu Ile Asn Ser
 1               5

<210> SEQ ID NO 156
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 156

Val Lys Ser Pro Phe Asp Cys Ser
 1               5

<210> SEQ ID NO 157
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 157

Val Arg Ser Pro Phe Asp Cys Ser
 1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 158

Asp Arg Ala Leu Ile Asn Ser
 1               5

<210> SEQ ID NO 159
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)

```
<223> OTHER INFORMATION: Cargo peptide

<400> SEQUENCE: 159

Ile Ser Gly Glu Phe Gly Leu Asp
 1               5

<210> SEQ ID NO 160
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 160

Cys Ser Gly Glu Phe Gly Leu Asp
 1               5

<210> SEQ ID NO 161
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Cargo peptide

<400> SEQUENCE: 161

Asp Asp Asp Ile Val Arg Lys
 1               5

<210> SEQ ID NO 162
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Cargo peptide

<400> SEQUENCE: 162

Asp Asp Ile Val Arg Lys
 1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 163

Ala Phe Asn Ser Tyr Glu Leu Gly Ser
 1               5

<210> SEQ ID NO 164
<211> LENGTH: 12
<212> TYPE: PRT
```

```
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(12)
<223> OTHER INFORMATION: Carrier peptide

<400> SEQUENCE: 164

Cys Tyr Gly Arg Lys Lys Arg Arg Gln Arg Arg
 1               5                  10

<210> SEQ ID NO 165
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide

<400> SEQUENCE: 165

Cys Ser Phe Asn Ser Tyr Glu Leu Gly Ser
 1               5                  10

<210> SEQ ID NO 166
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Carrier peptide

<400> SEQUENCE: 166

Tyr Gly Arg Lys Lys Arg Arg Gln Arg Arg
 1               5                  10

<210> SEQ ID NO 167
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(21)
<223> OTHER INFORMATION: Linear peptide

<400> SEQUENCE: 167

Glu Ala Val Ser Leu Lys Pro Thr Gly Gly Tyr Gly Arg Lys Lys Arg
 1               5                  10                  15

Arg Gln Arg Arg Arg
             20

<210> SEQ ID NO 168
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Carrier peptide
```

```
<400> SEQUENCE: 168

Cys Lys Leu Phe Ile Met Asn
1               5

<210> SEQ ID NO 169
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(20)
<223> OTHER INFORMATION: Cargo peptide

<400> SEQUENCE: 169

Gly Lys Leu Phe Ile Met Asn Leu Gly Tyr Gly Arg Lys Lys Arg
1               5                   10                  15

Gln Arg Arg Arg
            20

<210> SEQ ID NO 170
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(21)
<223> OTHER INFORMATION: Linear peptide

<400> SEQUENCE: 170

Gly Lys Leu Phe Ile Met Asn Leu Ser Gly Tyr Gly Arg Lys Lys Arg
1               5                   10                  15

Arg Gln Arg Arg Arg
            20

<210> SEQ ID NO 171
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(21)
<223> OTHER INFORMATION: Linear peptide

<400> SEQUENCE: 171

Gly Glu Glu Val Ile Arg Asn Ile Ser Gly Tyr Gly Arg Lys Lys Arg
1               5                   10                  15

Arg Gln Arg Arg Arg
            20

<210> SEQ ID NO 172
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(12)
<223> OTHER INFORMATION: Modified TAT carrier peptide
<220> FEATURE:
<221> NAME/KEY: SITE
<222> LOCATION: 1
```

```
<223> OTHER INFORMATION: Xaa = acetylated cysteine
<220> FEATURE:
<221> NAME/KEY: SITE
<222> LOCATION: 12
<223> OTHER INFORMATION: Xaa = amide-modified arginine

<400> SEQUENCE: 172

Xaa Tyr Gly Arg Lys Lys Arg Arg Gln Arg Arg Xaa
 1               5                   10
```

MODIFICATIONS OF PEPTIDE COMPOSITIONS TO INCREASE STABILITY AND DELIVERY EFFICIENCY

RELATED APPLICATIONS

This application is a divisional of U.S. application Ser. No. 12/017,985, filed Jan. 22, 2008, now U.S. Pat. No. 8,067,532 which claims the benefit of priority of U.S. Provisional Patent Application Ser. Nos. 60/881,419 and 60/945,285, all of which are incorporated herein by reference in their entirety.

REFERENCE TO SEQUENCE LISTING

A Sequence Listing is being submitted electronically via EFS in the form of a text file, created Nov. 28, 2011, and named "632008007US02seqlist.txt" (42977 bytes), the contents of which are incorporated herein by reference in their entirety.

1. Technical Field

This application relates to compositions and methods to improve carrier of biologically active agents into cells in living tissue. The compositions and methods comprise a PKC modulatory peptide conjugated to a modified tat peptide that imparts improved plasma stability to the conjugate, allowing more efficient uptake of the PKC modulatory peptide into cells.

2. Background Art

Research has produced many peptides that have potential as therapeutic compositions. Yet realizing and exploiting the full therapeutic potential of peptides directed against intracellular targets has yet to be achieved, for a variety of reasons. One of the most important of these is that most therapeutic peptides do not possess the ability to cross cell membranes to reach their therapeutic targets. One solution to this problem is the use of carrier peptides that act to ferry a cargo peptide into a target cell.

There are a number of notable examples of carrier peptides which are effective to facilitate the crossing of a target cell's membrane by a cargo peptide. One example is a peptide sequence derived from the TAT protein of the HIV virus. See U.S. Pat. No. 6,316,003, which is hereby incorporated by reference in its entirety. Another well known carrier peptide sequence is the "poly-Arg" sequence. See. e.g., U.S. Pat. No. 6,306,993.

In many cases, the use of a disulfide bond to link the carrier and cargo peptides, producing the therapeutic peptide construct, is an effective strategy to solve the problem of targeting soluble peptides to intracellular targets. One theory explaining the usefulness of disulfide bonds holds that once the carrier-cargo construct enters a target cell, the two peptides can separate through disulfide bond reduction. This separation in the intracellular environment may allow a greater diffusion of cargo peptides within the cell as opposed to other linkage mechanisms which maintain the carrier-cargo link. With this said, however, the administration of therapeutic peptides still suffers from numerous challenges, such as disulfide bond exchange, proteolytic degradation and efficiency of cellular uptake. Methods directed to controlling these issues will increase the stability and potency of therapeutic peptides.

One way to increase the potency of a therapeutic peptide comprising a carrier peptide disulfide bonded to a cargo peptide is to reduce disulfide bond exchange. Disulfide bond exchange reduces the amount of a carrier-cargo peptide construct in a given sample by allowing a carrier peptide to exchange its cargo peptide for another carrier peptide, thus resulting in a carrier-carrier construct and a cargo-cargo construct. The carrier-only construct will have no therapeutic effect. The cargo-cargo construct will have a tremendously reduced, if not completely eliminated effect, since the carrier peptide enables the delivery of the cargo to its intracellular target. As such, the problem of controlling disulfide bond exchange is important to maximizing the therapeutic potential of a carrier-cargo peptide construct.

Another problem facing the use of therapeutic peptides is proteolytic degradation. Peptides are notoriously unstable molecules and frequently labile to proteolytic attack when administered to a subject. Labile carrier peptides which degrade upon administration will reduce or even eliminate the efficacy of the cargo peptide because the cargo depends upon the carrier peptide to reach the intracellular target. Thus, methods to control or eliminate the labile nature of therapeutic peptides are also important to maximizing a carrier-cargo peptide's therapeutic potential.

Increasing the efficiency of cellular uptake of a therapeutic peptide is yet another problem which can reduce the efficacy or potency of a therapeutic peptide. Optimization of carrier peptide sequences and placement relative to the cargo peptide provide methods for increasing the stability and potency of therapeutic peptide constructs.

DISCLOSURE OF THE INVENTION

The disclosed invention relates to methods of preparing a therapeutic peptide composition comprising a carrier peptide and a PKC activity modulating cargo peptide, whereby the resulting therapeutic peptide compositions have increased stability and potency relative to an unmodified therapeutic peptide. One embodiment of the invention is a method of decreasing disulfide bond exchange in a therapeutic peptide composition, comprising providing a therapeutic peptide composition, which comprises a carrier peptide comprising a first cysteine residue and a PKC activity modulating cargo peptide comprising a second cysteine residue, wherein the carrier peptide and the cargo peptide are linked by a cysteine-cysteine disulfide bond between the first and second cysteine residues, and introducing at least one aliphatic residue immediately proximate to the first or second cysteine residues, or both, whereby the rate of disulfide bond exchange is decreased relative to an unmodified therapeutic peptide composition.

Another embodiment of the disclosed invention related to a method of decreasing proteolytic degradation of a therapeutic peptide composition, comprising providing a therapeutic peptide composition, which comprises a carrier peptide and a PKC activity modulating cargo peptide, and wherein the carrier peptide is linked to the cargo peptide, identifying a proteolytically labile site on the carrier peptide, the cargo peptide, or both peptides, and modifying the amino acid sequence at the labile site such that the rate of proteolytic degradation at the site is decreased relative to an unmodified therapeutic peptide composition.

Another embodiment of the disclosed invention relates to a method of increasing plasma stability of a therapeutic peptide composition, comprising providing a therapeutic peptide composition, which comprises a carrier peptide and a PKC activity modulating cargo peptide, and wherein the carrier peptide is linked to the cargo peptide, modifying the amino terminal, carboxy terminal or both residues of the carrier peptide, the cargo peptide, or both, such that the plasma stability of the therapeutic peptide composition is increased relative to an unmodified therapeutic peptide composition.

Compositions are also contemplated disclosed herein. One embodiment of the disclosed compositions comprises a protein kinase C (PKC) modulatory peptide composition. comprising a PKC modulatory peptide covalently linked to an intracellular carrier peptide, wherein the intracellular carrier peptide, the modulatory peptide, or both are modified at the N-terminus.

BRIEF DESCRIPTION OF THE DRAWINGS

FIG. 4 shows illustrate the conversion of a therapeutic peptide comprising a carrier peptide and a cargo peptide linked via a disulfide bond to a therapeutic peptide in linear form. This linear peptide (KP-01547) has been capped at its amino and carboxy termini and contains a short amino acid sequence linker.

FIG. 16 shows linear peptides KP-1680, KP-1681, KP-1633, and KP-1678.

FIG. 17A-D shows graphs of the percent of peptides remaining in test solutions over time.

MODES FOR CARRYING OUT THE INVENTION

Figure 1:
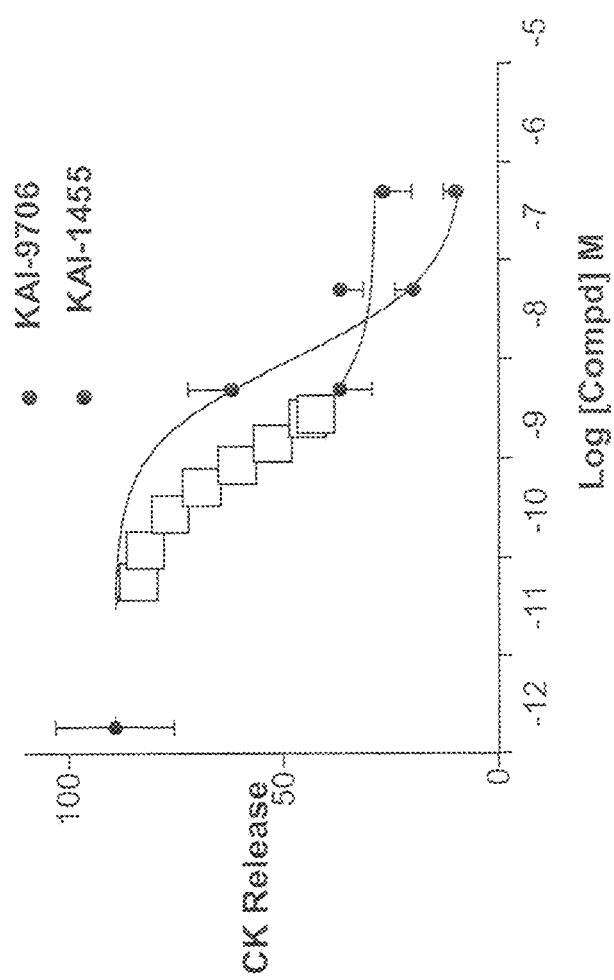
FIG. 1 shows a graph plotting CK release against concentrations of therapeutic peptides KA1-9706 and KA1-1455.

The disclosed invention relates to methods of modifying peptide compositions to increase stability and delivery efficiency. Specifically, the disclosed invention relates to methods to increase the stability and delivery efficiency of protein kinase C (PKC) modulatory peptide compositions. A "therapeutic peptide composition" comprises a "carrier peptide" and a "cargo peptide." A "carrier peptide" is a peptide or amino acid sequence within a peptide that facilitates the cellular uptake of the therapeutic peptide composition. The "cargo peptide" is a PKC modulatory peptide. Peptide modifications to either the carrier peptide, the cargo peptide, or both, which are described herein increase the stability and delivery efficiency of therapeutic peptide compositions by reducing disulfide bond exchange, physical stability, reducing proteolytic degradation, and increasing efficiency of cellular uptake.

Disulfide Bond Exchange.

A preferred embodiment of the disclosed therapeutic peptide compositions provides a cargo peptide coupled to a carrier peptide via a disulfide bond between two joining sulfur-containing residues, one in each peptide. The disulfide bond of this embodiment can be unstable whether the therapeutic peptide composition is in solution, lyophilized, precipitated, crystallized, or spray-dried, leading to carrier-cargo combinations to degrade to carrier-carrier compositions, which are inactive, and cargo-cargo compositions, which are also inactive and are frequently insoluble. The stability of the disclosed therapeutic peptide compositions is improved through the use of chemical modifications and by controlling the physical environment of the peptide compositions prior to use.

Chemical Modifications

The joining sulfur-containing residue can be placed anywhere in the sequence of the carrier or cargo peptides. For example, a preferred embodiment of the disclosed therapeutic peptide composition typically has the joining sulfur-containing residue at the amino terminus of the carrier and cargo peptides. The joining sulfur-containing residues can be placed at the carboxy termini of the peptides, or alternatively at the amino terminus of peptide and at the carboxy terminus of the other peptide. Additionally, the joining sulfur-containing residue can be placed anywhere within the sequence of either or both of the peptides. Placing the joining sulfur-containing residue within the carrier peptide, the cargo peptide, or both has been observed to reduce the rate of disulfide bond exchange.

An example of chemical modifications useful to stabilize the disulfide bonds of the therapeutic peptide compositions involves optimizing the amino acid residue or residues immediately proximate to the sulfur-containing residues used to join the carrier and cargo peptide. A preferred method of stabilizing the disulfide bond involves placing an aliphatic residue immediately proximate to the sulfur-containing residue in the carrier and/or cargo peptides. Aliphatic residues include alanine, valine, leucine and isoleucine. Thus, when the joining sulfur-containing residue is placed at the amino terminus of a peptide, an aliphatic residue is placed at the penultimate amino terminal position of the peptide to reduce the rate of disulfide bond exchange. When the joining sulfur-containing residue is located at the carboxy terminus of a peptide, an aliphatic residue is placed at the penultimate carboxy terminal position of the peptide to reduce the rate of disulfide bond exchange. When the joining sulfur-containing residue is located within the sequence of a peptide, the aliphatic residue can be place at either the amino terminal or carboxy terminal side of the residue, or at both sides.

A variety of sulfur-containing residues are contemplated for use with the presently disclosed invention. Cysteine and cysteine analogs can also be used as the joining cysteine residues in the peptide composition. Particular cysteine analogs include D-cysteine, homocysteine, alpha-methyl cysteine, mercaptopropionic acid, mercaptoacetic acid, penicillamine, acetylated forms of those analogs capable of accepting an acetyl group, and cysteine analogs modified with other blocking groups. For example, the use of homocysteine, acetylated homocysteine, penicillamine, and acetylated penicillamine in the cargo, the carrier, or both peptides have been shown to stabilize the peptide composition and decrease disulfide bond exchange. Alpha-methyl cysteine inhibits disulfide degration because the base-mediated abstraction of the alpha hydrogen from one cysteine is prevented by the presence of the sulfur atom. Cargo/carrier peptide conjugates joined by disulfide bonds have been shown to be more resistant to glutathione reduction than unmodified peptides. Other cysteine analogs are also useful as joining cysteines. Similarly, stereoisomers of cysteine will inhibit disulfide bond exchange.

Disulfide bond exchange can be eliminated completely by linking the carrier and cargo peptides to form a single, linear peptide. This method is discussed below.

Physical Stability

Figure 10:
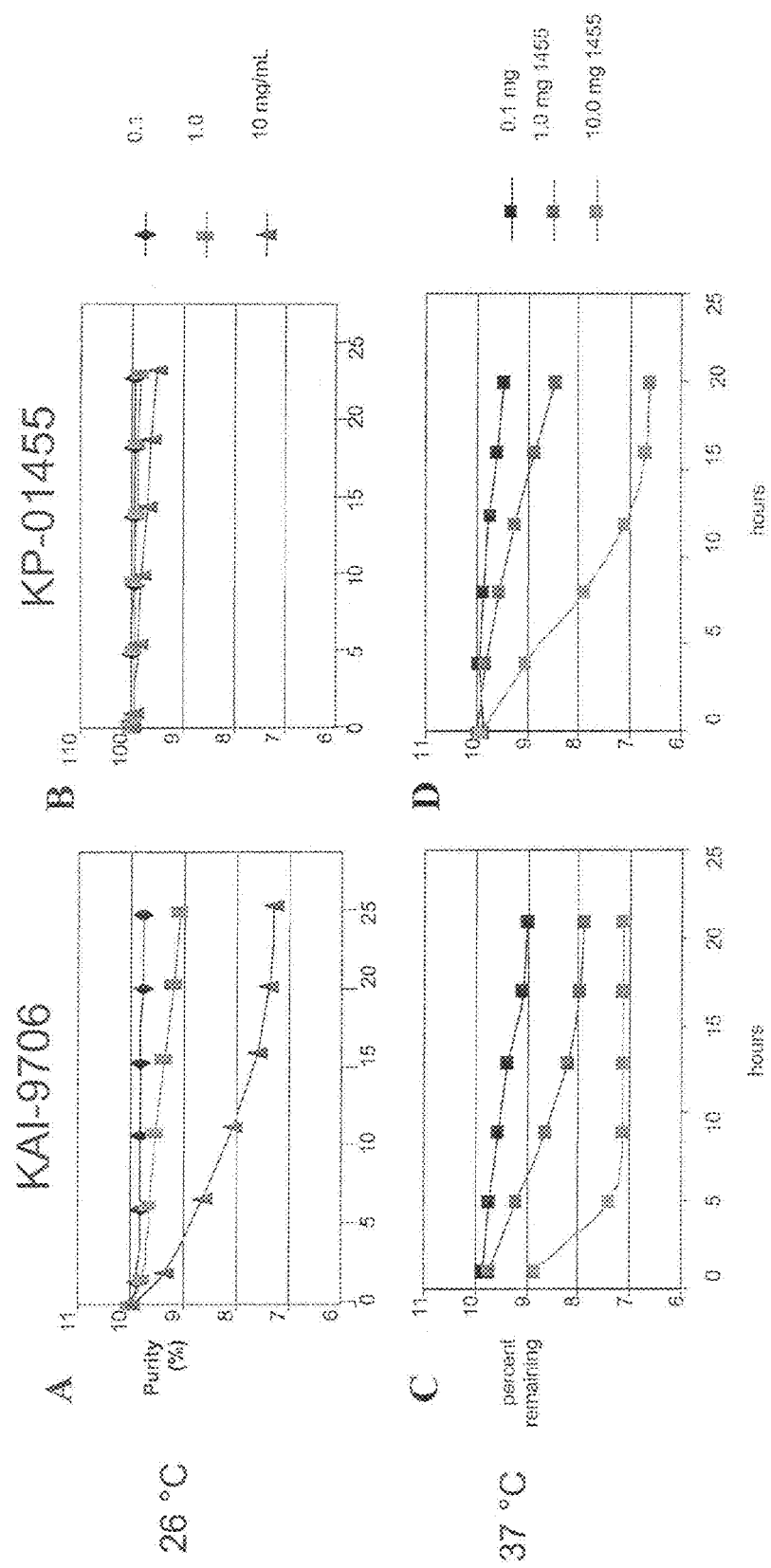
FIG. 10A-10D shows graphs illustrating the impact of temperature on the stability KA1-9706 at 26° C. (10A) and 37° C. (10B), and on KA1 1455 at 26° C. (10C) and 37° C. (10D).

The physical environment of the disulfide has an effect on stability. As shown (in part) in FIG. 10, stability increases in solution as the pH of the solution decreases (acidic environment better than basic), the temperature of the solution decreases, and as the concentration of the peptide composition in solution decreases. In the lyophilized form, stability increases as the pH decreases, the temperature decreases, and the ratio of the peptide composition to excipient increases. Preferred excipients are discussed in U.S. patent application Ser. No. 11/240,962, filed Sep. 30, 2005, which is hereby incorporated by reference in its entirety.

The unexpected "excipient effect" was most pronounced for mannitol, which is a highly crystalline excipient. Using less crystalline excipients (such as sucrose) or even using no excipient, showed much less dependency on peptide composition quantity. Although not wishing to be bound or limited by any theory, it is thought that use of a non-crystalline excipient creates an amorphous matrix, which helps prevent intermolecular associations. Theoretically, in a crystalline matrix the peptide composition is excluded and forced to the walls of the vial, perhaps causing high local concentrations. With low amount of API the resulting thin film has high peptide-glass contact area and the silica is destabilizing.

Figure 14:
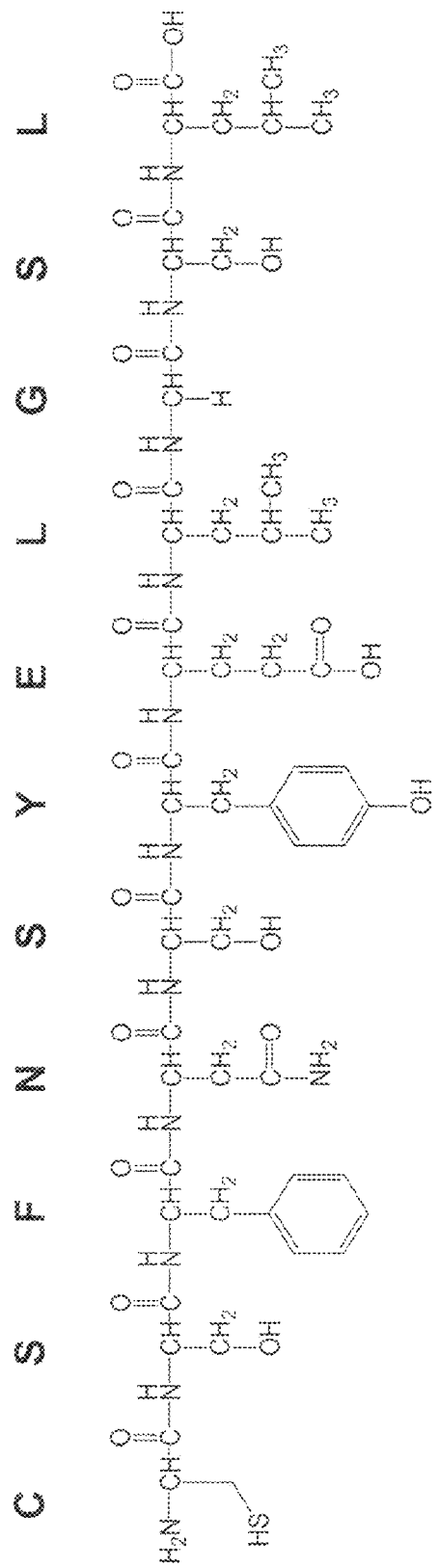
FIG. 14 shows a illustrates the cargo peptide of SEQ ID NO:33 with a cysteine residue at the amino terminus of the peptide.

A number of factors impact the efficiency with which a therapeutic peptide composition is taken up by a target cell. For example, the solubility of a therapeutic peptide impacts the efficiency with which the peptide is taken up by a target cell. In turn, the amino acid sequence of a carrier or cargo peptide largely determines that solubility the peptide compositions in which they are used. Some peptides, particularly cargo peptides, will contain hydrophobic residues. (e.g., Phe, Tyr, Leu), with regular spacing which allows for intramolecular interactions by a "zipper" mechanism leading to aggregation. An example of such a potentially problematic peptide is shown in FIG. 14. The illustrated sequence is believed to form a beta-strand in the V1 domain of δPKC. Such peptides have the tendency to form insoluble deposits.

The solubility of such peptides can be improved by making certain modifications to the cargo peptide sequence. For example, the introduction of solubilizing groups at amino and or carboxy termini or on internal residues, such as hydrating groups, like polyethylene glycol (PEG), highly charged groups, like quaternary ammonium salts, or bulky, branched chains of particular amino acid residues will improve the solubility of peptides like the one illustrated in FIG. 14. Additionally, those hydrophobic side chains that are shown not to be required for activity can be eliminated by deletion or substitution with a conservative or non-interfering residue, such as an alanine, glycine, or serine, thus improving the solubility of the peptides.

Proteolytic Degradation: Plasma Stability

Blood and plasma contain proteases which can degrade the protein kinase C modulatory peptides disclosed herein or the carrier peptides which facilitate the cellular uptake of the peptide composition, or both. One method to decrease proteolytic degradation of the carrier or cargo peptides is to mask the targets of the proteases presented by the therapeutic peptide composition.

Once the therapeutic peptide enters the plasma of a subject, it become vulnerable to attack by peptidases. Strategies are provided which address peptide degradation caused by exopeptidases (any of a group of enzymes that hydrolyze peptide bonds formed by the terminal amino acids of peptide chains) or endopeptidases (any of a group of enzymes that hydrolyze peptide bonds within the long chains of protein molecules). Exopeptidases are enzymes that cleave amino acid residues from the amino or carboxy termini of a peptide or protein, and can cleave at specific or non-specific sites. Endopeptidases, which cleave within an amino acid sequence, can also be non-specific, however endopeptidases frequently recognize particular amino sequences (recognition sites) and cleaves the peptide at or near those sites.

One method of protecting peptide compositions from proteolytic degradation involves the "capping" the amino and/or carboxy termini of the peptides. The term "capping" refers to the introduction of a blocking group to the terminus of the peptide via a covalent modification. Suitable blocking groups serve to cap the termini of the peptides without decreasing the biological activity of the peptides. Acetylation of the amino termini of the described peptides is a preferred method of protecting the peptides from proteolytic degradation. Other capping moieties are possible. The selection of acylating moiety provides an opportunity to "cap" the peptide as well as adjust the hydrophobicity of the compound. For example, the hydrophobicity increases for the following acyl group series: formyl, acetyl, propanoyl, hexanoyl, myristoyl, and are also contemplated as capping moieties. Amidation of the carboxy termini of the described peptides is also a preferred method of protecting the peptides from proteolytic degradation.

Protecting peptides from endopeptidases typically involves identification and elimination of an endopeptidase recognition site from a peptide. Protease recognition cites are well known to those of ordinary, skill in the art. Thus it is possible to identify a potential endoprotease recognition site and then eliminating that site by altering the amino acid sequence within the recognition site. Residues in the recognition sequence can be moved or removed to destroy the recognition site. Preferably, a conservative substitution is made with one or more of the amino acids which comprise an identified protease recognition site. The side chains of these amino acids possess a variety of chemical properties. For the purposes of the present discussion, the most common amino acids are categorized into 9 groups, listed below. Substitution within these groups is considered to be a conservative substitution.

| Conservative Amino Acid Substitution | |
|---|---|
| Small/Aliphatic residues: | Gly, Ala, Val, Leu, Ile |
| Cyclic Imino Acid: | Pro |
| Hydroxyl Residues: | Ser, Thr |
| Acidic Residues: | Asp, Glu |
| Amide Residues: | Asn, Gln |

-continued

| Conservative Amino Acid Substitution | |
|---|---|
| Basic Residues: | Lys, Arg |
| Imidazole Residue: | His |
| Aromatic Residues: | Phe, Tyr, Trp |
| Sulfur-Containing Residues: | Met, Cys |

Efficiency of Cellular Uptake

In addition to the modifications discussed above, improve utility for the disclosed therapeutic peptide compositions can be achieved by altering the linkage of the carrier and cargo peptides. For example, in one embodiment, carrier and cargo peptides are linked by a peptide bond to form a linear peptide. Stability and potency of the therapeutic peptides can also be increased through the construction of peptide multimers, wherein a plurality of cargo peptides is linked to one or more carrier peptides. An additional embodiment of the invention involving a cleavable linker sequence is also discussed.

Linear Peptides

Another strategy to improve peptide composition stability involves joining the cargo and carrier peptides into a single peptide as opposed to joining the peptides via a disulfide bond. For example, in the embodiment shown in FIG. 4A, the cargo peptide (SEQ ID NO:13) linked via amino terminal cysteines. A linear version of the cargo and carrier peptides is shown in FIG. 4B, where the cargo and carrier peptides are linked via a short dipeptide linker (e.g., Ser-Gly). This linker is exemplary.

In the example illustrated, the C-terminus of cargo is linked to the N-terminus of the carrier via the linker. However, the other possible permutations are also contemplated, including linking the peptide via there C-termini, their N-termini, and where the carrier peptide is located at the N-terminal portion of the peptide composition.

Additionally, the steps discussed above to stabilize a disulfide bond linked peptide composition can also be used with a linear, where appropriate. For example, the linear peptide composition shown in FIG. 4B has been capped at both its amino and carboxy termini. Moreover sequences within the peptide can be scrambled or substituted with D-amino acids.

Figure 7:
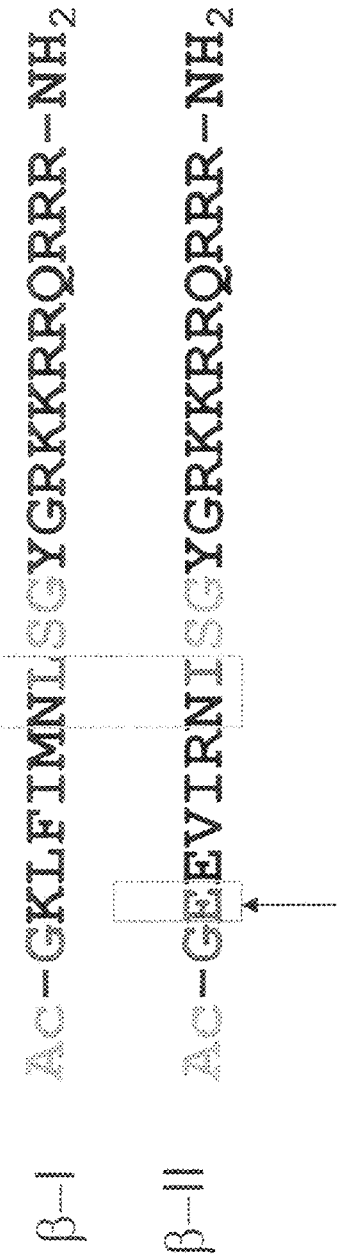
FIG. 7 shows illustrated two linear peptides.
Figure 8:
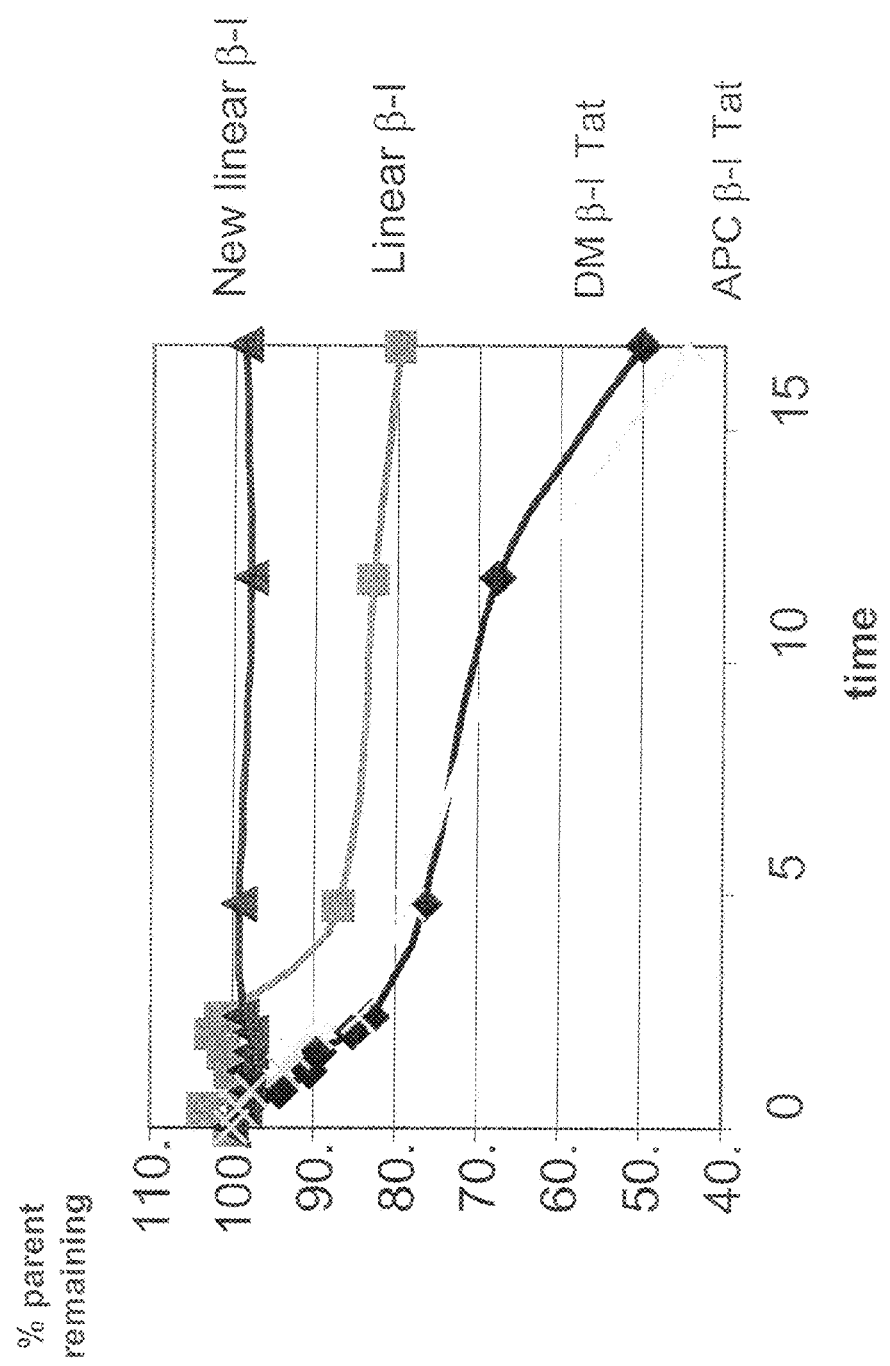
FIG. 8 shows a graph comparing the stability of various PKC-$\beta_I$ therapeutic peptides over time.
Figure 9:
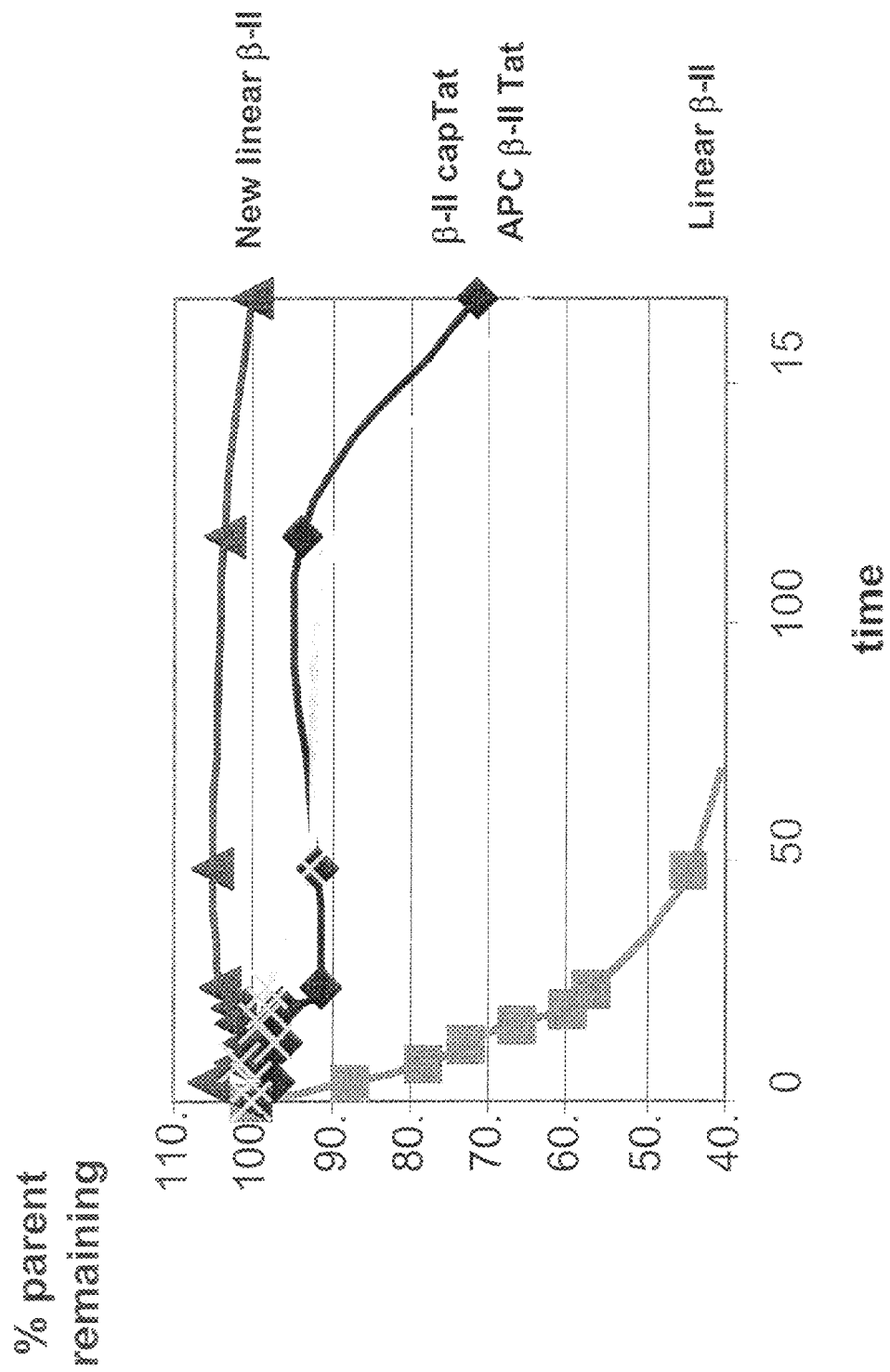
FIG. 9 shows a graph a graph comparing the stability of various PKC-$\beta_{II}$ therapeutic peptides over time.

As shown in FIG. 7, deamination of Asn at position 7 of the β-I had been observed to cause significant instability in the linearized version of the peptide composition linked by Asn-Gly. Changing the Gly to Leu stabilized this linear peptide composition. Similarly, deamination of the Gln residue at position 2 of the linear β-II composition was observed to cause significant instability. Substitution with Glu improved stability of the linear composition. Data comparing the modified versions of these peptides is shown in FIGS. 8 and 9.

Without being limited to any particular theory, it is thought that deamination results from the attack of the alpha or main-chain amide HN—C-terminal to the Asn residue on the side-chain amide of Asn, generating the cyclic aspartamide intermediate which can hydrolyze to an aspartic acid moiety. Increasing the size of the residue C-terminal to Asn is thought to increase the steric hinderance on the main-chain amide, significantly slowing deamidation.

Peptide Multimers

Figure 15:
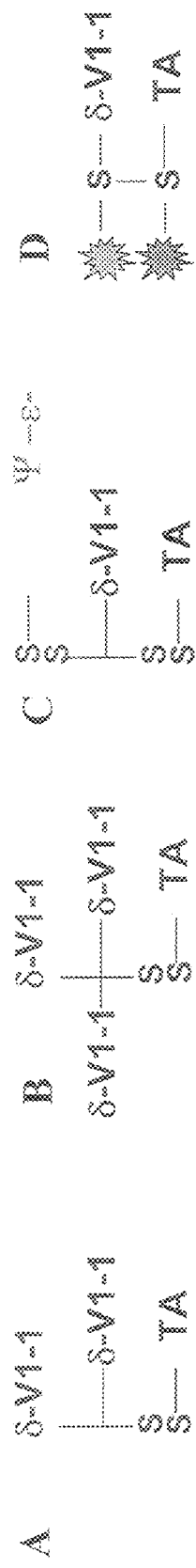
FIG. 15A-15D show four different possible configurations of therapeutic peptide multimers.
Figure 17A:
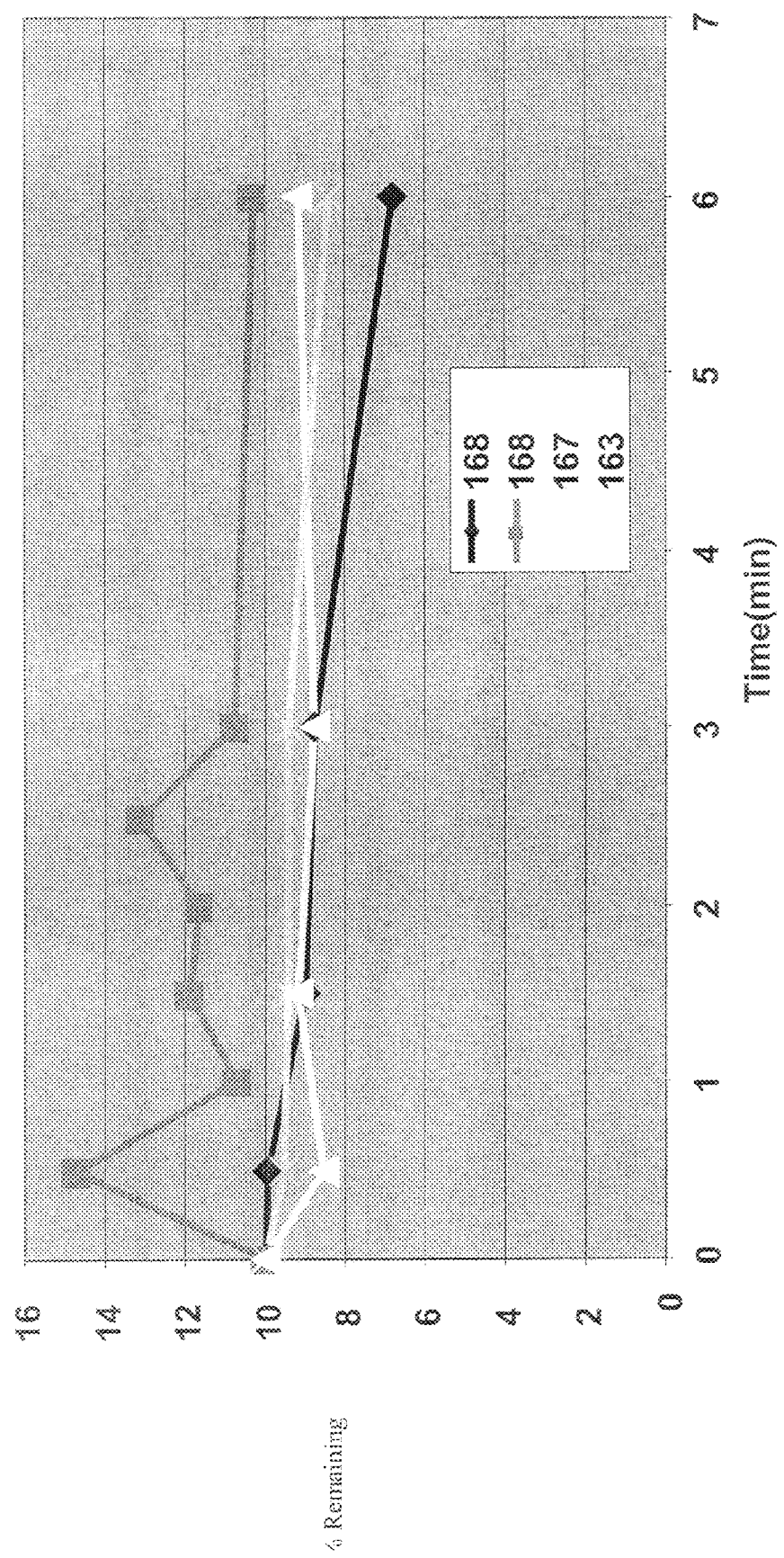
Figure 17D:
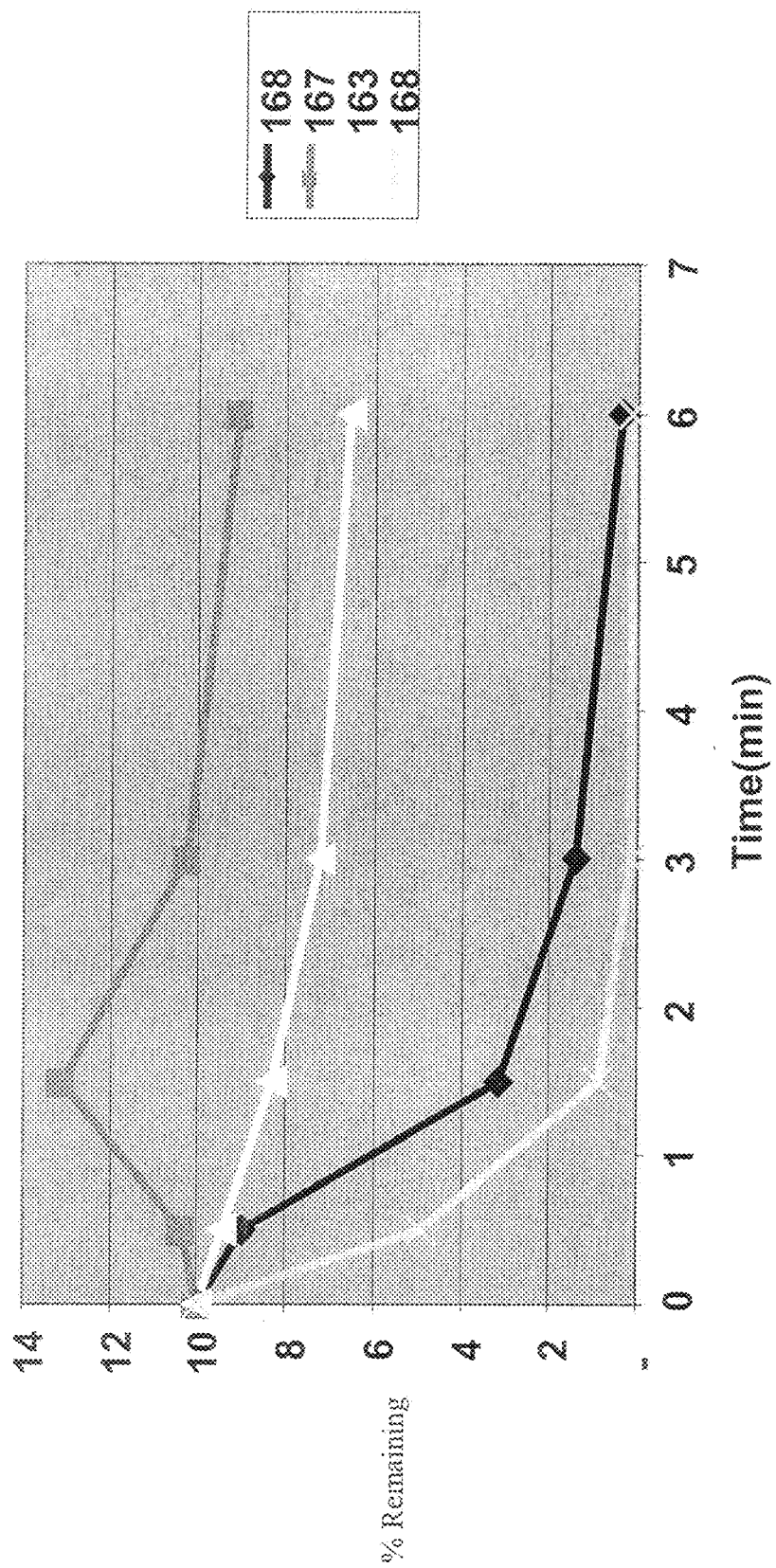

Another method of improving stability and potency is available by forming multimers with a plurality of cargo peptides associated with one or more carrier peptides. Examples of such formulations are shown in FIG. 15. Branched, multivalent peptide compositions will increase avidity, potency and stability of the compositions. By engineering cleavage sites or other release mechanisms into the multimer compositions, the multiple conjugates can release nearly simultaneously, PKC modulatory cargo peptides inside a target cell. An example of multimeric peptides is discussed in Yu et al. JBC 275(6):3943-9 (2000).

Cleavable Sequence

Typically the carrier and cargo are linked by a linkage that can be cleaved by ubiquitous enzymes such as esterases, amidases, and the like. It is assumed that the concentration of such enzymes is higher inside cells rather than in the extra-cellular milieu. Thus, once the conjugate is inside a cell, it is more likely to encounter an enzyme that can cleave the linkage between cargo and carrier. The enzyme can thus release the biologically active cargo inside a cell, where it presumably is most useful.

Protein Kinase C Modulatory Peptides

The term protein kinase C modulatory peptide refers to a peptide derived from a PKC isozyme- and/or variable region. Various PKC isozyme- and variable region-specific peptides have been described and can be used with the presently disclosed invention. Preferably, the PKC modulatory peptide is a V1, V3 or V5-derived peptide. (The terminology "V1" and "C2" are synonymous.) The following US Patents or Patent Applications describe a variety of suitable peptides that can be used with the presently disclosed invention: U.S. Pat. Nos. 5,783,405, 6,165,977, 6,855,693, US2004/0204364, US2002/0150984, US2002/0168354, US2002/057413, US2003/0223981, US2004/0009922 and U.S. Pat. No. 10/428,280, each of which are incorporated herein by reference in their entirety. Table 1 provides a listing of preferred PKC modulatory peptides for use with the present invention.

TABLE 1

| Cargo Peptides derived from PKC isozymes | | |
|---|---|---|
| Peptide | SEQ ID NO. | Sequence |
| αV3-1 | SEQ ID NO: 2 | I-P-E-G-D-E-E-G |
| αV5-1 | SEQ ID NO: 3 | Q-L-V-I-A-N |
| αV5-1.1 | SEQ ID NO: 4 | G-L-G-A-E-N |
| αV5-1.2 | SEQ ID NO: 5 | A-R-G-A-E-N |
| αV5-1.3 | SEQ ID NO: 6 | C-G-K-G-A-E-N |
| αV5-1.4 | SEQ ID NO: 7 | C-G-K-G-A-E-N |
| βC2-1 | SEQ ID NO: 8 | K-Q-K-T-K-T-I-K |
| βC2-2 | SEQ ID NO: 9 | M-D-P-N-G-L-S-D-P-Y-V-K-L |
| βC2-3 | SEQ ID NO: 10 | I-P-D-P-K-S-E |
| βC2-4 | SEQ ID NO: 11 | S-L-N-P-E-W-N-E-T |
| βV3-1 | SEQ ID NO: 12 | V-P-P-E-G-S-E-A |
| β1V5-1 | SEQ ID NO: 13 | K-L-F-I-M-N |
| β1V5-2 | SEQ ID NO: 14 | R-D-K-R-D-T-S |
| β1V5-2.1 | SEQ ID NO: 15 | C-A-R-D-K-R-D-T-S |
| β1V5-2.2 | SEQ ID NO: 16 | G-R-D-K-R-D-T-S |
| β1V5-2.3 | SEQ ID NO: 17 | A-R-D-K-R-D-T-S |
| β1V5-3 | SEQ ID NO: 18 | A-R-D-K-R-D-T-S-N-F-D-K |
| β1V5-4 | SEQ ID NO: 19 | A-G-F-S-Y-T-N-P-E-F-V-I-N-V |

TABLE 1-continued

Cargo Peptides derived from PKC isozymes

| Peptide | SEQ ID NO. | Sequence |
|---|---|---|
| β11V5-1 | SEQ ID NO: 20 | Q-E-V-I-R-N |
| β11V5-2 | SEQ ID NO: 21 | C-G-R-N-A-E |
| β11V5-3 | SEQ ID NO: 22 | A-C-G-R-N-A-E |
| β11V5-3.1 | SEQ ID NO: 23 | A-C-G-K-N-A-E |
| β11V5-4 | SEQ ID NO: 24 | K-A-C-G-R-N-A-E |
| β11V5-5 | SEQ ID NO: 25 | C-G-R-N-A-E-N |
| β11V5-6 | SEQ ID NO: 26 | A-C-G-R-N-A-E |
| β11V5-7 | SEQ ID NO: 27 | S-F-V-N-S-E-F-L-K-P-E-V-L-S |
| γV3-1 | SEQ ID NO: 28 | V-A-D-A-D-N-C-S |
| γV5-1 | SEQ ID NO: 29 | G-R-S-G-E-N |
| γV5-1.1 | SEQ ID NO: 30 | G-L-S-G-E-N |
| γV5-2 | SEQ ID NO: 31 | R-L-V-L-A-S |
| γV5-3 | SEQ ID NO: 32 | P-C-G-R-S-G-E-N |
| δV1-1 | SEQ ID NO: 33 | C-S-F-N-S-Y-E-L-G-S-L |
| Leu-Truncate | SEQ ID NO: 165 | C-S-F-N-S-Y-E-L-G-S |
| δV1-1.1 | SEQ ID NO: 34 | S-F-N-S-Y-E-L-G-S-L |
| δV1-1.2 | SEQ ID NO: 35 | T-F-N-S-Y-E-L-G-S-L |
| δV1-1.3 | SEQ ID NO: 36 | A-F-N-S-N-Y-E-L-G-S-L |
| δV1-1.4 | SEQ ID NO: 37 | S-F-N-S-Y-E-L-G-T-L |
| δV1-1.5 | SEQ ID NO: 38 | S-T-N-S-Y-E-L-G-S-L |
| δV1-1.6 | SEQ ID NO: 39 | S-F-N-S-F-E-L-G-S-L |
| δV1-1.7 | SEQ ID NO: 40 | S-N-S-Y-D-L-G-S-L |
| δV1-1.8 | SEQ ID NO: 41 | S-F-N-S-Y-E-L-P-S-L |
| δV1-1.9 | SEQ ID NO: 42 | T-F-N-S-Y-E-L-G-T-L |
| δV1-1.10 | SEQ ID NO: 43 | S-F-N-S-Y-E-I-G-S-V |
| δV1-1.11 | SEQ ID NO: 44 | S-F-N-S-Y-E-V-G-S-I |
| δV1-1.12 | SEQ ID NO: 45 | S-F-N-S-Y-E-L-G-S-V |
| δV1-1.13 | SEQ ID NO: 46 | S-F-N-S-Y-E-L-G-S-I |
| δV1-1.14 | SEQ ID NO: 47 | S-F-N-S-Y-E-I-G-S-L |
| δV1-1.15 | SEQ ID NO: 48 | S-F-N-S-Y-E-V-G-S-L |
| δV1-1.16 | SEQ ID NO: 49 | A-F-N-S-Y-E-L-G-S-L |
| δV1-1.17 | SEQ ID NO: 50 | Y-D-L-G-S-L |
| δV1-1.18 | SEQ ID NO: 51 | F-D-L-G-S-L |
| δV1-1.19 | SEQ ID NO: 52 | Y-D-I-G-S-L |
| δV1-1.20 | SEQ ID NO: 53 | Y-D-V-G-S-L |
| δV1-1.21 | SEQ ID NO: 54 | Y-D-L-P-S-L |
| δV1-1.22 | SEQ ID NO: 55 | Y-D-L-G-L-L |
| δV1-1.23 | SEQ ID NO: 56 | Y-D-L-G-S-I |
| δV1-1.24 | SEQ ID NO: 57 | Y-D-L-G-S-V |
| δV1-1.25 | SEQ ID NO: 58 | I-G-S-L |
| δV1-1.26 | SEQ ID NO: 59 | V-G-S-L |
| δV1-1.27 | SEQ ID NO: 60 | L-P-S-L |
| δV1-1.28 | SEQ ID NO: 61 | L-G-L-L |
| δV1-1.29 | SEQ ID NO: 62 | L-G-S-I |
| δV1-1.30 | SEQ ID NO: 63 | L-G-S-V |
| δV1-2 | SEQ ID NO: 64 | A-L-S-T-E-R-G-K-T-L-V |
| δV1-2.1 | SEQ ID NO: 65 | A-L-S-T-D-R-G-K-T-L-V |
| δV1-2.2 | SEQ ID NO: 66 | A-L-T-S-D-R-G-K-T-L-V |
| δV1-2.3 | SEQ ID NO: 67 | A-L-T-T-D-R-G-K-S-L-V |
| δV1-2.4 | SEQ ID NO: 68 | A-L-T-T-D-R-P-K-T-L-V |
| δV1-2.5 | SEQ ID NO: 69 | A-L-T-T-D-R-G-R-T-L-V |
| δV1-2.6 | SEQ ID NO: 70 | A-L-T-T-D-K-G-K-T-L-V |
| δV1-2.7 | SEQ ID NO: 71 | A-L-T-T-D-K-G-K-T-L-V |
| δV1-3 | SEQ ID NO: 72 | V-L-M-R-A-A-E-E-P-V |
| δV1-4 | SEQ ID NO: 73 | Q-S-M-R-S-E-D-E-A-K |
| δV1-5 | SEQ ID NO: 163 | A-F-N-S-Y-E-L-G-S |
| δV3-1 | SEQ ID NO: 74 | Q-G-F-E-K-K-T-G-V |
| δV3-2 | SEQ ID NO: 75 | D-N-N-G-T-Y-G-K-I |
| δV5-1 | SEQ ID NO: 76 | K-N-L-I-D-S |
| δV5-2 | SEQ ID NO: 77 | V-K-S-P-R-D-Y-S |
| δV5-2.1 | SEQ ID NO: 78 | V-K-S-P-C-R-D-Y-S |
| δV5-2.2 | SEQ ID NO: 79 | I-K-S-P-R-L-Y-S |
| δV5-3 | SEQ ID NO: 80 | K-N-L-I-D-S |
| δV5-4 | SEQ ID NO: 81 | P-K-V-K-S-P-R-D-Y-S-N |
| εV1-1 | SEQ ID NO: 82 | N-G-L-L-K-I-K |
| εV1-2 | SEQ ID NO: 83 | E-A-V-S-L-K-P-T |
| εV1-3 | SEQ ID NO: 84 | L-A-V-F-I-I-D-A-P-I-G-Y |
| εV1-4 | SEQ ID NO: 85 | D-D-F-V-A-N-C-T-I |
| εV1-5 | SEQ ID NO: 86 | W-I-D-L-E-P-E-G-R-V |
| εV1-6 | SEQ ID NO: 87 | H-A-V-G-P-R-P-Q-T-F |
| εV1-7 | SEQ ID NO: 88 | N-G-S-R-H-F-E-D |
| εV1-7.1 | SEQ ID NO: 89 | H-D-A-P-I-G-Y-D |
| εV1-7.2 | SEQ ID NO: 90 | H-D-A-P-I-G |
| εV1-7.3 | SEQ ID NO: 91 | H-D-A-A-I-G-Y-D |
| εV1-7.4 | SEQ ID NO: 92 | H-D-A-P-I-P-Y-D |
| εV1-7.5 | SEQ ID NO: 93 | H-N-A-P-I-G-Y-D |

TABLE 1-continued

Cargo Peptides derived from PKC isozymes

| Peptide | SEQ ID NO. | Sequence |
|---|---|---|
| εV1-7.6 | SEQ ID NO: 94 | H-A-A-P-I-G-Y-D |
| εV1-7.7 | SEQ ID NO: 95 | A-D-A-P-I-G-Y-D |
| εV1-7.8 | SEQ ID NO: 96 | H-D-A-P-A-G-Y-D |
| εV1-7.9 | SEQ ID NO: 97 | H-D-A-P-I-G-A-D |
| εV1-7.10 | SEQ ID NO: 98 | H-D-A-P-I-A-Y-D |
| εV1-7.11 | SEQ ID NO: 99 | H-D-A-P-I-G-Y-A |
| εV3-1 | SEQ ID NO: 100 | S-S-P-S-E-E-D-R-S |
| εV3-2 | SEQ ID NO: 101 | P-C-D-Q-E-I-K-E |
| εV3-3 | SEQ ID NO: 102 | E-N-N-I-R-K-A-L-S |
| εV3-4 | SEQ ID NO: 103 | G-E-V-R-Q-G-Q-A |
| εV5-1 | SEQ ID NO: 104 | E-A-I-V-K-Q |
| εV5-2 | SEQ ID NO: 105 | I-K-T-K-R-D-V |
| εV5-2.1 | SEQ ID NO: 106 | I-K-T-K-R-L-I |
| εV5-3 | SEQ ID NO: 107 | C-E-A-I-V-K-Q |
| εV5-4 | SEQ ID NO: 108 | T-K-R-D-V-N-N-F-D-Q |
| ζV1-1 | SEQ ID NO: 109 | V-R-L-K-A-H-Y |
| ζV1-2 | SEQ ID NO: 110 | V-D-S-E-G-D |
| ζV1-3 | SEQ ID NO: 111 | V-F-P-S-I-P-E-Q |
| ζV3-1 | SEQ ID NO: 112 | S-Q-E-P-P-V-D-D-K-N-E-D-A-D-L |
| ζV3-2 | SEQ ID NO: 113 | I-K-D-D-S-E-D |
| ζV3-3 | SEQ ID NO: 114 | P-V-I-D-G-M-D-G-I |
| ζV5-1 | SEQ ID NO: 115 | E-D-A-I-K-R |
| ζV5-1.1 | SEQ ID NO: 116 | E-D-A-I-R |
| ζV5-2 | SEQ ID NO: 117 | I-T-D-D-Y-G-L-D |
| ζV5-2.1 | SEQ ID NO: 118 | I-T-D-D-Y-G-D-L |
| ζV5-3 | SEQ ID NO: 119 | D-D-Y-G-L-D-N |
| ηV1-1 | SEQ ID NO: 120 | N-G-Y-L-R-V-R |
| ηV1-2 | SEQ ID NO: 121 | E-A-V-G-L-Q-P-T |
| ηV1-3 | SEQ ID NO: 122 | L-A-V-F-H-E-T-P-L-G-Y |
| ηV1-4 | SEQ ID NO: 123 | D-F-V-A-N-C-T-L |
| ηV1-5 | SEQ ID NO: 124 | W-V-D-L-E-P-E-G-K-V |
| ηV1-6 | SEQ ID NO: 125 | H-S-L-F-K-K-G-H |
| ηV1-7 | SEQ ID NO: 126 | T-G-A-S-D-T-F-E-G |
| ηV5-1 | SEQ ID NO: 127 | E-G-H-L-P-M |
| ηV5-1.1 | SEQ ID NO: 128 | E-G-H-D-P-M |
| ηV5-2 | SEQ ID NO: 129 | I-K-S-R-E-D-V-S |
| ηV5-3 | SEQ ID NO: 130 | V-R-S-R-E-D-V-S |

TABLE 1-continued

Cargo Peptides derived from PKC isozymes

| Peptide | SEQ ID NO. | Sequence |
|---|---|---|
| ηV5-4 | SEQ ID NO: 131 | P-R-I-K-S-R-E-D-V |
| λV1-1 | SEQ ID NO: 132 | H-Q-V-R-V-K-A-Y-Y-R |
| λV1-2 | SEQ ID NO: 133 | Y-E-L-N-K-D-S-E-L-L-I |
| λV3-1 | SEQ ID NO: 134 | M-D-Q-S-S-M-H-S-D-H-A-Q-T-V-I |
| λV3-2 | SEQ ID NO: 135 | L-D-Q-V-G-E-E |
| λV3-3 | SEQ ID NO: 136 | E-A-M-N-T-R-E-S-G |
| λV5-1 | SEQ ID NO: 137 | D-D-I-V-R-K |
| μV5-2 | SEQ ID NO: 138 | V-K-L-C-D-F-G-F |
| μV5-2.1 | SEQ ID NO: 139 | I-R-L-C-D-F-A-F |
| μV5-3 | SEQ ID NO: 140 | Q-V-K-L-C-D-F-G-F-A |
| μV1-1 | SEQ ID NO: 141 | M-S-V-P-P-L-L-R-P |
| μV1-2 | SEQ ID NO: 142 | K-F-P-E-C-G-F-Y-G-L-Y |
| μV3-1 | SEQ ID NO: 143 | D-P-D-A-D-Q-E-D-S |
| μV3-2 | SEQ ID NO: 144 | S-K-D-T-L-R-K-R-H |
| μV3-3 | SEQ ID NO: 145 | I-T-L-F-Q-N-D-T-G |
| μV3-4 | SEQ ID NO: 146 | G-S-N-S-I-I-K-D-I-S |
| μV5-1 | SEQ ID NO: 147 | S-D-S-P-E-A |
| ΘV1-1 | SEQ ID NO: 148 | G-L-S-N-F-D-C-G |
| ΘV1-2 | SEQ ID NO: 149 | Y-V-E-S-E-N-G-Q-M-Y-I |
| ΘV1-3 | SEQ ID NO: 150 | I-V-K-G-K-N-V-D-L-I |
| ΘV1-4 | SEQ ID NO: 151 | D-M-N-E-F-E-T-E-G-F |
| ΘV3-1 | SEQ ID NO: 152 | C-S-I-K-N-E-A-R-L |
| ΘV3-2 | SEQ ID NO: 153 | G-K-R-E-P-Q-G-I-S |
| ΘV3-3 | SEQ ID NO: 154 | D-E-V-D-K-M-C-H-L |
| ΘV5-1 | SEQ ID NO: 155 | R-A-L-I-N-S |
| ΘV5-2 | SEQ ID NO: 156 | V-K-S-P-F-D-C-S |
| ΘV5-2.1 | SEQ ID NO: 157 | V-R-S-P-F-D-C-S |
| ΘV5-3 | SEQ ID NO: 158 | D-R-A-L-I-N-S |
| ιV5-1 | SEQ ID NO: 159 | I-S-G-E-F-G-L-D |
| ιV5-1.1 | SEQ ID NO: 160 | C-S-G-E-F-G-L-D |
| ιV5-2 | SEQ ID NO: 161 | D-D-D-I-V-R-K |
| ιV5-3 | SEQ ID NO: 162 | D-D-I-V-R-K |

TABLE 2

Carrier Peptides

| | | |
|---|---|---|
| TAT Carrier Peptide | SEQ ID NO: 166 | YGRKKRRQRRR |

TABLE 2-continued

Carrier Peptides

| TAT Carrier Peptide with N-terminal Cys | SEQ ID NO: 164 | CYGRKKRRQRRR |
|---|---|---|

Other examples of carries include octa-Arg, octa-D-Arg, and *Antennapedia* derived peptides, which are known in the art.

The following examples are offered to illustrate but not to limit the invention.

Example 1

Exopeptidase Protection: Plasma Stability of Capped Peptides

Plasma stability of capped peptides was compared. KA1-9706 was modified stepwise at its amino and carboxy termini. Plasma stability as measured by the percent of peptide composition remaining after 15 minutes. The results are provided in Table 2.

TABLE 2

Plasma Stability of KAI-9706

|  |  | cargo | | | |
|---|---|---|---|---|---|
|  |  | H—OH | Ac—OH | H—NH$_2$ | Ac—NH$_2$ |
| carrier | H—OH | 1 | 1 | 0 | 0 |
|  | Ac—OH | 57 | nd | nd | 48 |
|  | H—NH$_2$ | 60 | nd | nd | 51 |
|  | Ac—NH$_2$ | 92 | 93 | 90 | 90 |

% parent remaining at 15 mins
$t_{1/2}$ in rat plasma = 40-45 mins for longest-lived derivatives The data provided above shows that the peptide composition, comprising unmodified cargo and carrier peptides, was the least stable. Moreover, protection of the carrier peptide alone failed to increase the half life of the peptide composition in plasma. Moreover, modification of the cargo peptide with the carrier peptide unmodified had no apparent effect on half-life stability in plasma. However, the addition of protecting groups to the carrier peptide, whether at the amino or carboxy termini lead to a marked and nearly equivalent increase in plasma stability for the peptide composition. Protection of both groups in the carrier peptide provided additional protection. Interestingly, protection of the cargo peptide had little or no effect on the stability of the composition.

Example 2

Effect of D-Peptides on Plasma Stability

KA1-9706 was engineered with D-amino acids to determine their impact on peptide composition stability. Unmodified KA1-9706 was compared to a peptide composition with the same amino acid sequence, however the amino acids used were d-enantiomers instead of l-amino acids. A retro-inverso version and a scrambled version of the peptide composition were also prepared. The data from the experiment is shown in Table 3.

TABLE 3

Plasma Stability of KAI-9706

|  |  | cargo | | | |
|---|---|---|---|---|---|
|  |  | All-L | All-D | scrambled | R/I |
| carrier | All-L | 1 | 0 | 2 |  |
|  | All-D | 88 | 100 | 67 |  |
|  | R/I |  |  |  | 100 |

% parent remaining at 15 mins

Modification of the carrier showed the great propensity in improving the half life of the composition while modification of the cargo showed little effect.

Example 3

Capped KA1-9706 Maintains in Vitro Potency

Capping the carrier peptide portion KA1-9706 (KA1-1455) was shown to increase the plasma half life of the peptide composition. The ability of the capped composition to inhibit ischemic damage in a rat heat model (Langendorff Assay) was evaluated versus the uncapped form. The results are shown in FIG. 1.

Example 4

Capped KA1-9706 Shows Increased Potency

Figure 2:
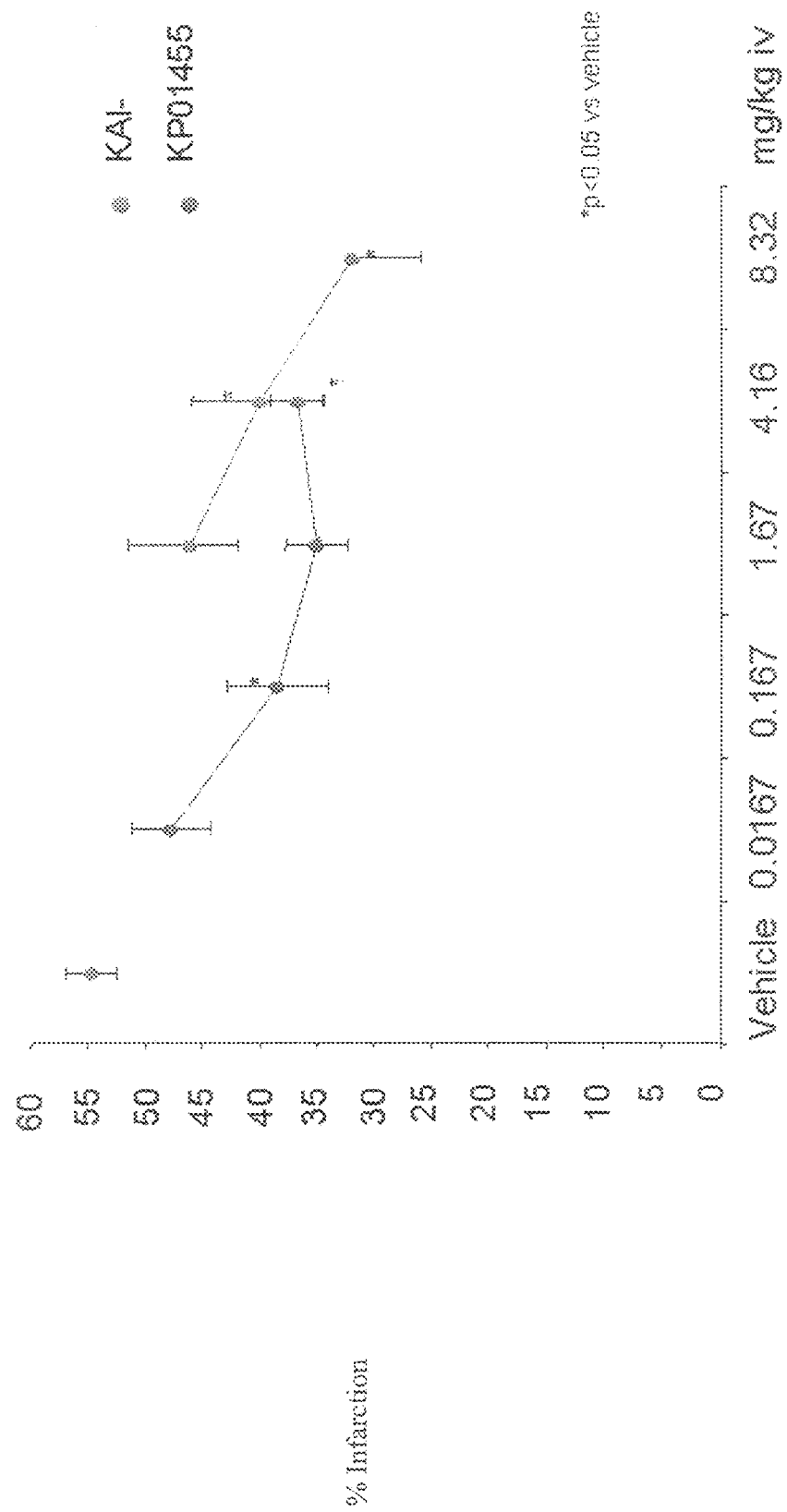
FIG. 2 shows a graph plotting percent infarction against increasing concentrations of therapeutic peptides KA1-9706 and KA1-1455.

KA1-1455 was tested in a stroke model. As shown in FIG. 2, the capped version of the peptide composition provided increased protection to brain tissue as judged by percent infract. This data shows that significant protection of brain tissue was achieved at lower doses.

Example 5

Peptide Stability is Increased Regardless of Species

Figure 3:
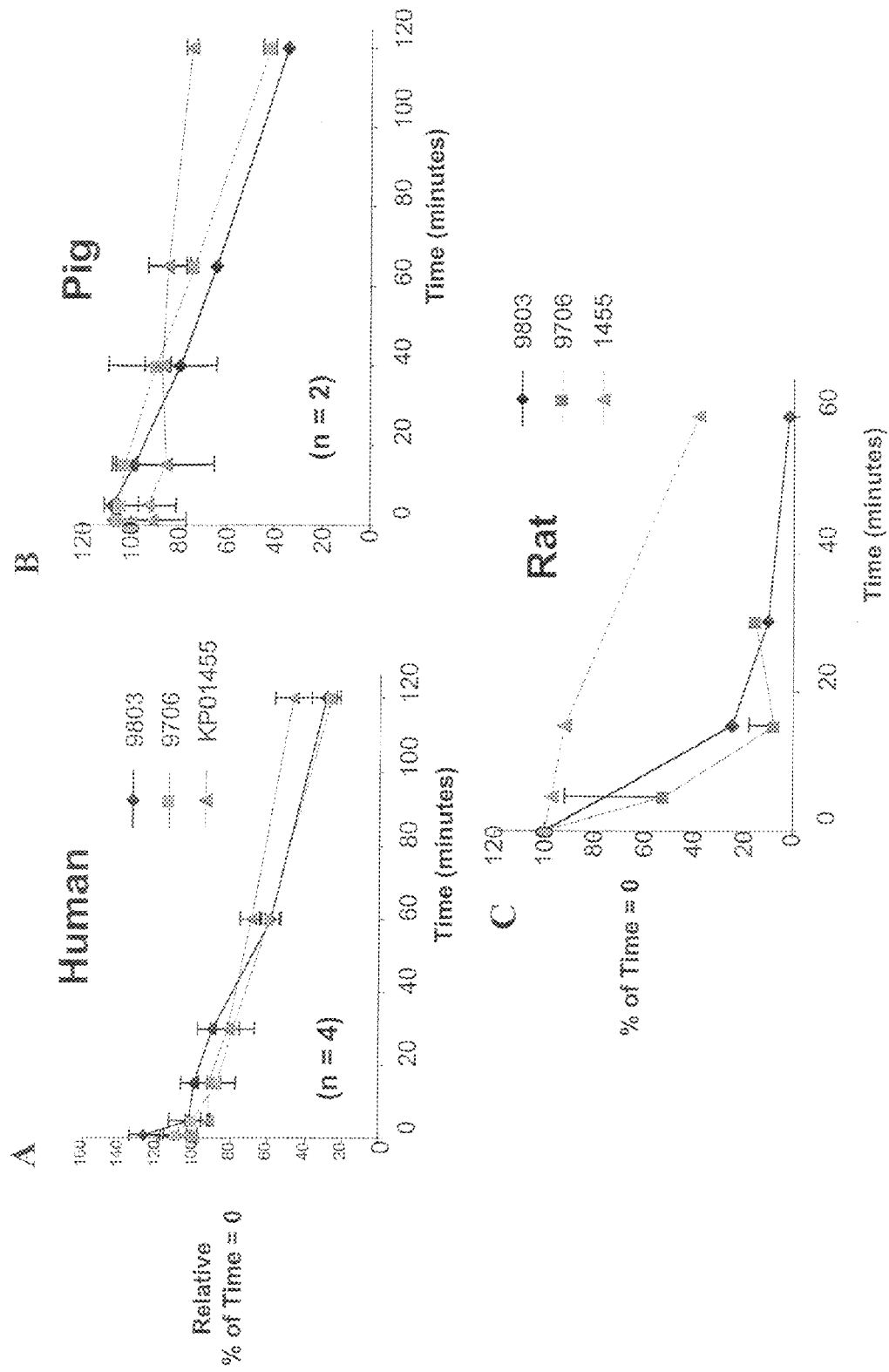
FIGS. 3A-3B show graphs plotting percent of intact therapeutic peptides KA1-9803. KA1-9706, and KA1-1455, surviving over time in human serum (3A), pig serum (3B), and rat serum (3C).

The stability of modified KA1-9706 peptide (KA1-1455) was compared against KA1-9706 and KA1-9803 in human (FIG. 3A), pig (FIG. 3B) and rat serum (FIG. 3C). The capped version, KA1-1455, showed increased plasma stability in all three species.

Example 6

Capped KA1-9706 Shows Increased Potency

KA1-1455 was tested in a stroke model. As shown in FIG. 2, the capped version of the peptide composition provided increased protection to brain tissue as judged by percent infract. This data shows that significant protection of brain tissue was achieved at lower doses.

Example 7

Peptide Stability is Increased Regardless of Species

The stability of modified KA1-9706 peptide (KA1-1455) was compared against KA1-9706 and KA1-9803 in human (FIG. 3A), pig (FIG. 3B) and rat serum (FIG. 3C). The capped version, KA1-1455, showed increased plasma stability in all three species.

Example 8

Stability of Linear Peptides

Figure 5:
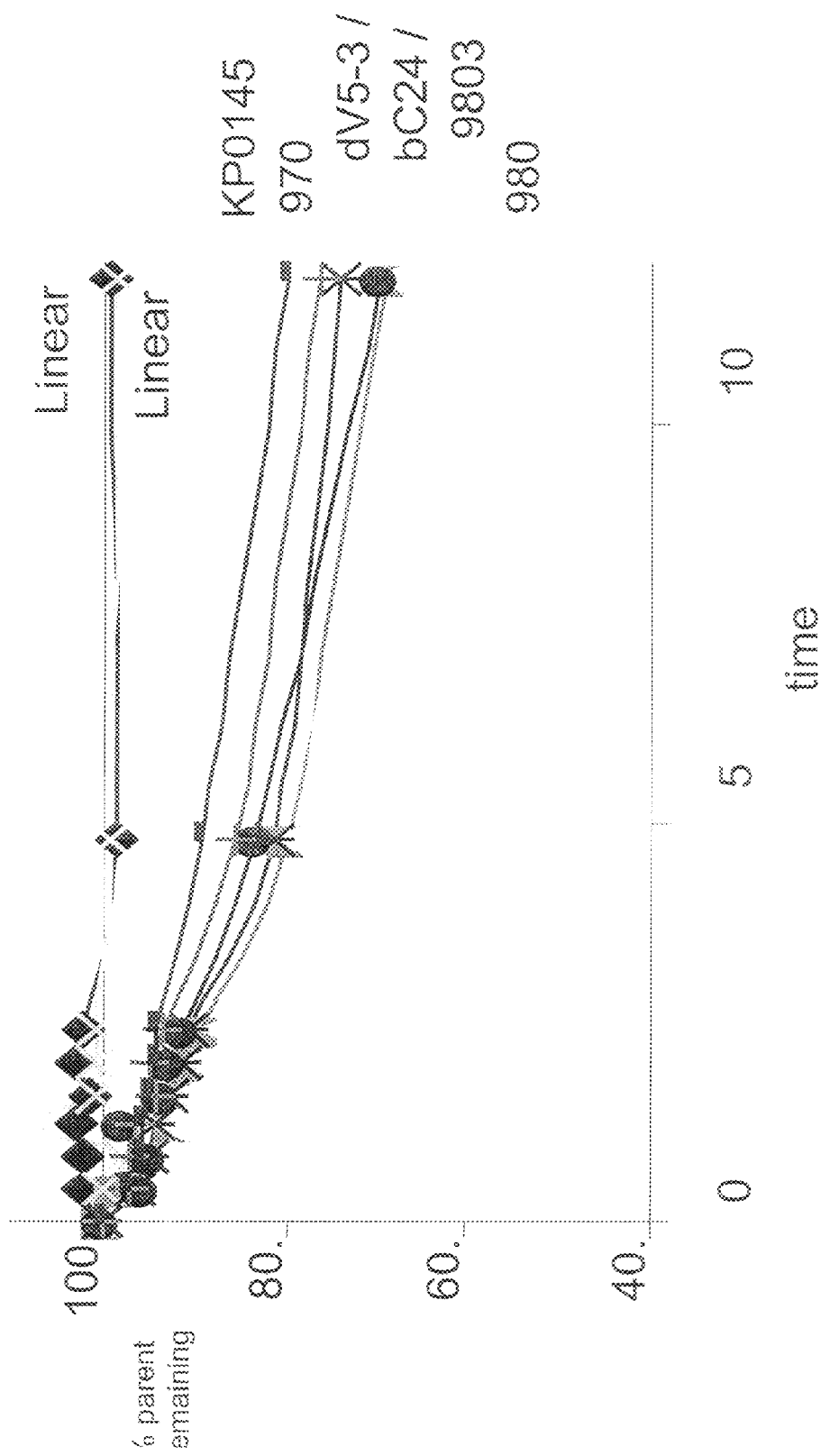
FIG. 5 shows a graph plotting percent of intact therapeutic peptides (linear and non-linear) over time (days).

Linear versions of KA1-9803 and BC2-4 were constructed to evaluate their stability relative to disulfide bond linked versions of these and other peptide compositions. The peptides were placed in solution at 0.1 mg/ml in PBS (pH 7.4) at 37° C. As shown in FIG. 5, the linear versions of KA1-9803 and BV2-4 showed increased stability.

Example 9

Figure 6:
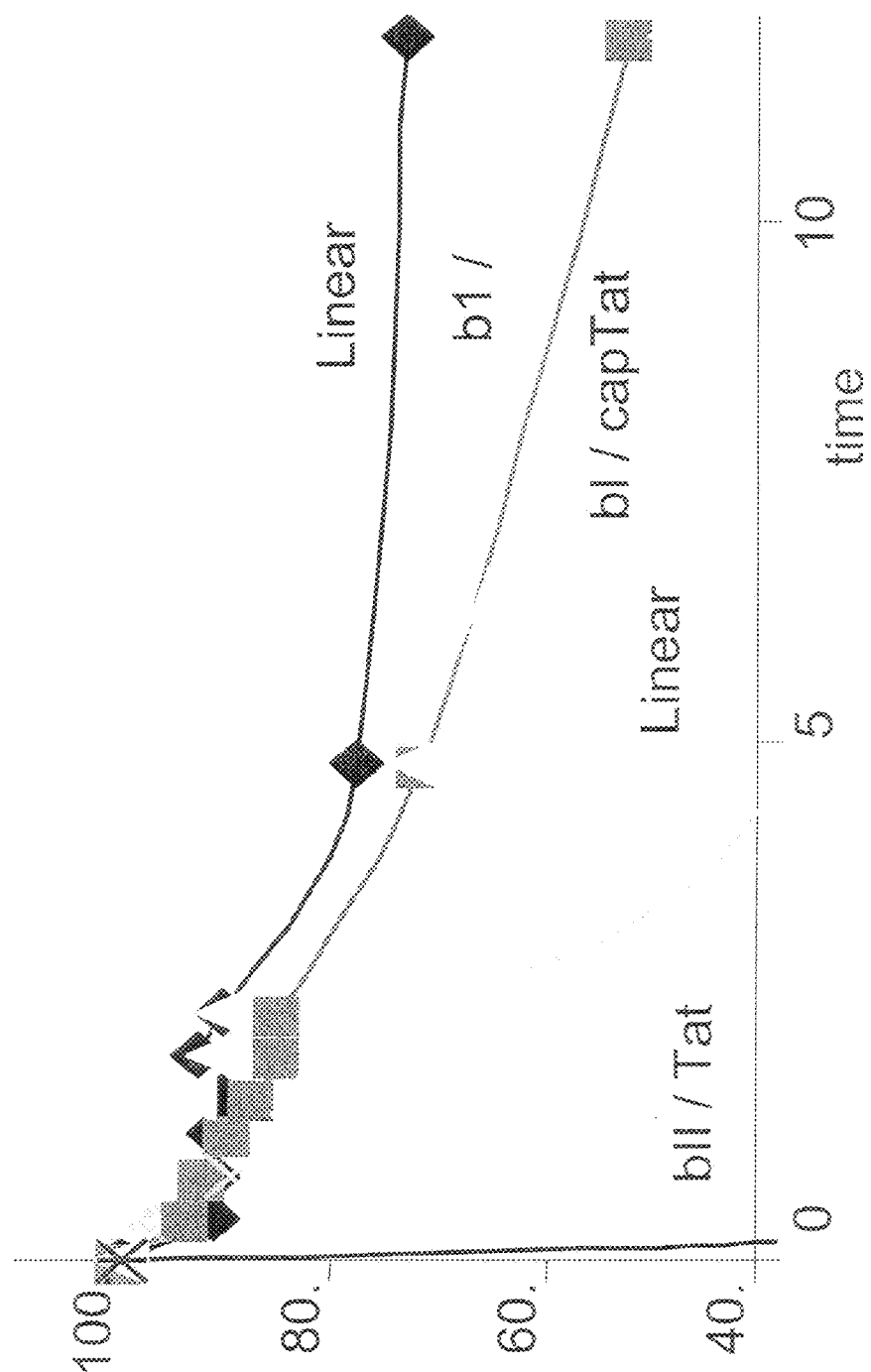
FIG. 6 shows a graph comparing the stability of therapeutic peptides over time (days).

Linear PKC-$\beta_I$ and PKC-$\beta_{II}$ Peptide Compositions Show Increased Stability Over Disulfide Linked Compositions Linear and disulfide bond linked versions of PKC-$\beta_I$ and PKC-$\beta_{II}$ peptide compositions were incubated under the conditions described in Example 8. As can be seen in FIG. 6, the linear forms of the PKC-$\beta_I$ and PKC-$\beta_{II}$ peptides showed increased stability as compared to their non-linear counterparts.

Example 10

Improved Stability of Linear PKC-$\beta_I$ and PKC-$\beta_{II}$ Peptide Compositions The linear versions of PKC-$\beta_I$ and PKC-$\beta_{II}$ peptide compositions showed improved stability but were also the subject of deamination reactions. In particular, the Asn residues at position 7 of the β-I and β-II peptides and the Gln at position 2 of the β-II peptide. These linear peptide compositions were modified by substituting the Gly immediately C-terminal to the Asn with either Leu in the β-I peptide composition or Gly to Ile in the β-II peptide composition. The Gln at position 2 of the β-II peptide composition was also substituted with a Glu residue. The stability of the peptides was studied under the conditions described in Example 8. As shown in FIGS. 8 and 9, the amino acid substitutions discussed above served to stabilize these linear peptide compositions.

Example 11

KA1-9803 Derivative (KA1-1355) Maintains Potency

Figure 11:
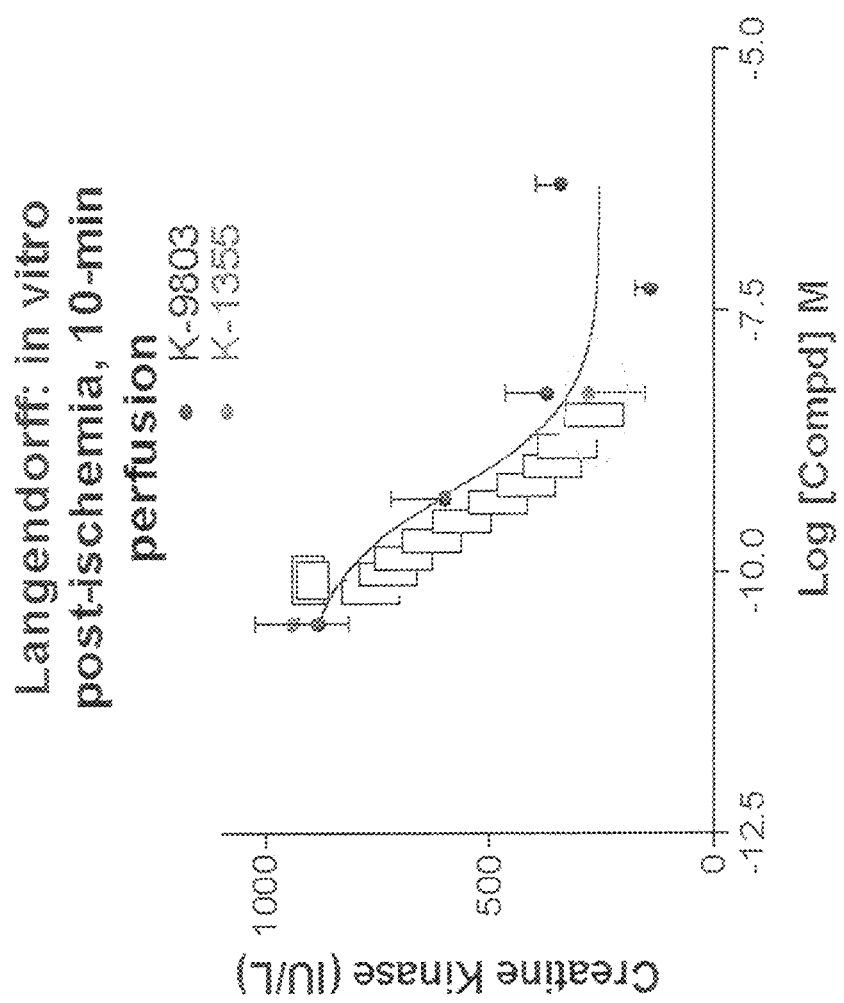
FIG. 11 shows a graph plotting creatine kinase release in the presence of increasing concentrations of KA1-9803 or KA1-1355 peptides in a Langendorff in vitro post-ischemia assay, with 10 minutes perfusion.

A truncated version of KA1-9803, KA1-1355, in which the carboxy terminal leucine was removed was tested for potency. Stability studies with KA1-1355 showed that deletion of the C-terminal Leu residue increased the stability of this cargo peptide. Potency of the derivative peptide composition was compared to that of the full length version, KA1-9803 in a Langendorff in vitro post-ischemia model. The results of the experiment are shown in FIG. 11. As shown, KA1-1355 (the modified version of KA1-9803) is still capable of protecting cardiac tissue from ischemia with potency comparable to that of the full length KA1-9803.

Example 12

Optimization of KA1-9803 to Produce KA1-1479

Figure 12:
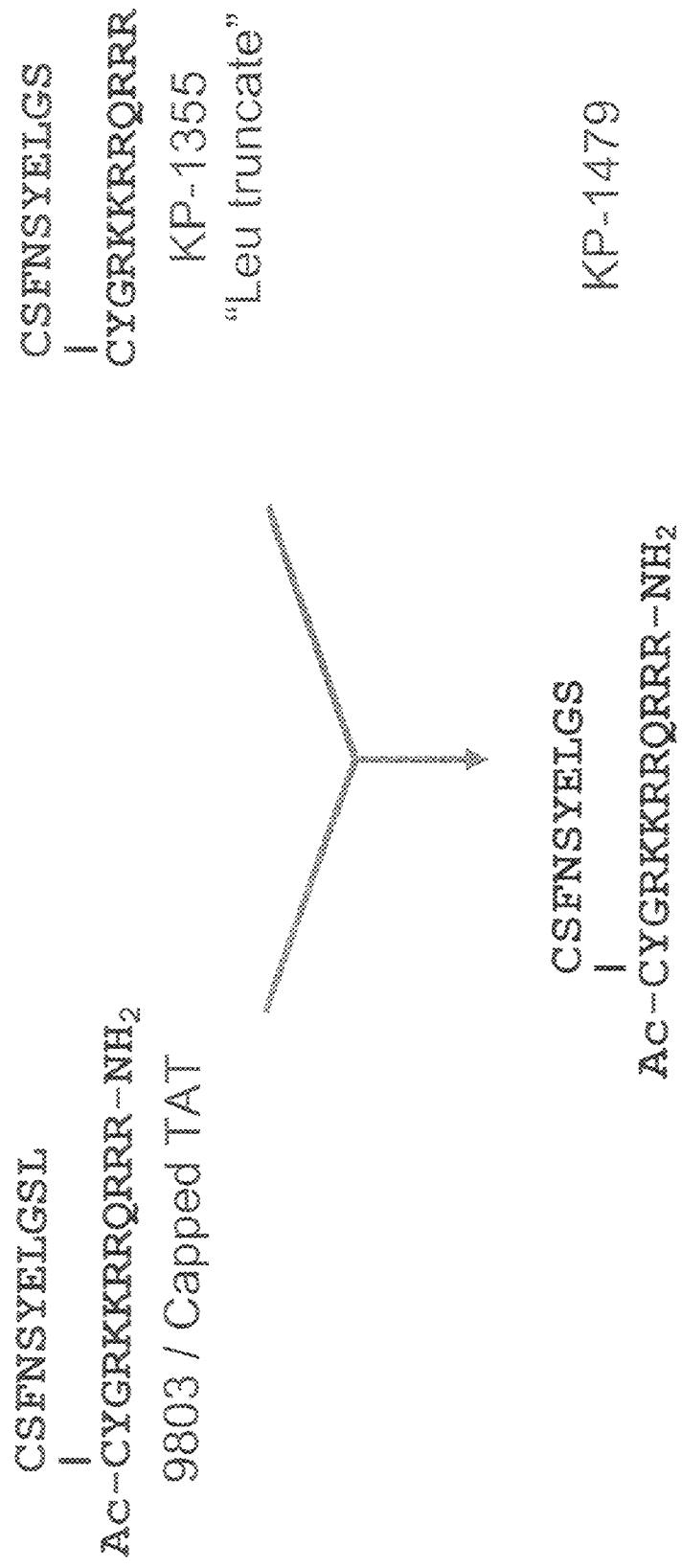
FIG. 12 shows an illustration depicting the construction of KA1-1479.

Having demonstrated that truncation of the cargo peptide of KA1-9803 had little or now effect on potency, while stabilizing the peptide composition. As illustrated in FIG. 12, a capped version of the TAT carrier peptide was bound to the truncated cargo peptide of KA1-1355, producing KA1-1479, which comprises a truncated 9803 cargo peptide and a fully capped TAT carrier peptide.

Figure 13:
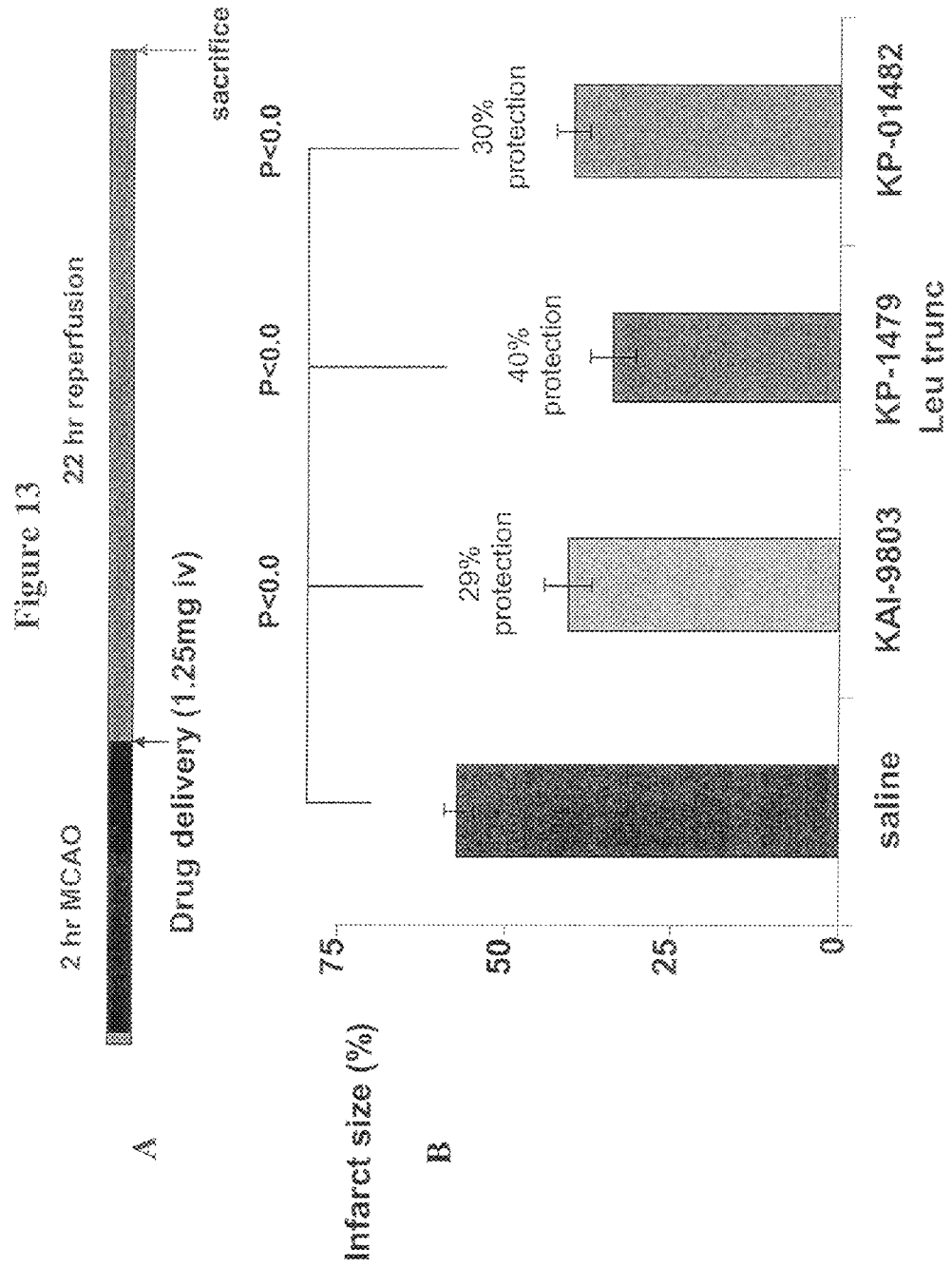
FIGS. 13A and 13B show bar graphs of results from a reperfusion study, wherein 13A illustrates the time line of events during the experiment and 13B shows a bar graph illustrating the protective properties of various therapeutic peptides (KA1-9803, KA1-1479, and KA1-1482).

The modified KA1-1479, KA1-9803 and KA1-1482 peptide compositions were assayed in a rat middle cerebral artery occlusion (MCAO) stroke model to determine the ability of the peptide compositions to inhibit infarct size. The rats were subjected to a 2 hour period of cerebral arterial occlusion. Each of the peptide compositions or saline was administered to the test animals immediately prior to a 22 hour reperfusion period, after which time the animals were sacrificed and the infarct size was measured. As shown in FIG. 13, the modified KA1-1479 peptide composition showed an increased ability to retard infarct size as compared to KA1-9803. KP-01482 has a cargo sequence (CELGSLQAEDD) linked to a TAT peptide with a N-Term Cys, which is capped at both ends and disulfide conjugated to the cargo.

Example 13

In Vitro Biological Stability of a Series of Linear Epsilon PKC Inhibitors

The effect of N-terminal acetylation and C-terminal amidation on compound stability in plasma and serum from rat and human was studied. The linear peptides examined are shown in FIG. 16. The compounds were tested in the plasma/serum at a concentration of 100 µg/ml. The solutions were incubated at room temperature, precipitated with 5% TCA, and then the supernatant was neutralized with ammonium acetate. The peptides were then analyzed by LC/MS. As can be seen from the data in FIGS. 17A-17D, all the tested compounds were relatively stable in human plasma but KP-1633 and KP-1678, containing C-terminal amides, showed increased stability in human serum. N-terminal acetylation alone did not stabilize the peptides. Interestingly, the amino acid sequence of KP-1680 and its degradation products indicated that the metabolized forms of the peptide showed sequential cleavage of arginine residues from the C-terminus. Carboxypeptidase N activity in the serum but not the plasma could account for the difference in observed stability. The plasma samples were collected with EDTA, which is known to inhibit this zinc metalloprotease.

I claim:

1. A linear therapeutic peptide, comprising:
a carrier peptide and a PKC activity modulating peptide,
wherein the carrier peptide and the cargo peptide are linked by a peptide bond,
and optionally a linker positioned between the PKC activity modulating peptide and the carrier peptide, wherein the carrier peptide and the PKC peptide are each linked to the linker by a peptide bond;
wherein the carrier peptide comprises the amino acid sequence YGRKKRRQRRR (SEQ ID NO:166);
and wherein the linear peptide is amidated at the C-terminus.

2. The linear peptide according to claim 1, wherein the PKC activity modulating peptide is selected from the group consisting of SFNSYELGSL (SEQ ID NO:34), CSFNSYELGSL (SEQ ID NO:33), EAVSLKPT (SEQ ID NO:83), KLFIMN (SEQ ID NO:13) and QEVIRN (SEQ ID NO:20).

* * * * *